United States Patent
Mor et al.

(10) Patent No.: US 9,693,927 B2
(45) Date of Patent: Jul. 4, 2017

(54) DEVICE AND METHODS OF TREATING NEUROLOGICAL DISORDERS

(71) Applicant: APOS—MEDICAL AND SPORTS TECHNOLOGIES LTD., Herzliya (IL)

(72) Inventors: Amit Mor, Rehovot (IL); Avi Elbaz, Dimona (IL)

(73) Assignee: APOS—Medical and Sports Technologies Ltd., Herzliya (IL)

( * ) Notice: Subject to any disclaimer, the term of this patent is extended or adjusted under 35 U.S.C. 154(b) by 28 days.

(21) Appl. No.: 14/363,506

(22) PCT Filed: Dec. 10, 2012

(86) PCT No.: PCT/IB2012/057124
§ 371 (c)(1),
(2) Date: Jun. 6, 2014

(87) PCT Pub. No.: WO2013/084212
PCT Pub. Date: Jun. 13, 2013

(65) Prior Publication Data
US 2015/0119767 A1    Apr. 30, 2015

Related U.S. Application Data

(60) Provisional application No. 61/568,200, filed on Dec. 8, 2011.

(51) Int. Cl.
| | |
|---|---|
| *A61H 3/00* | (2006.01) |
| *A43B 7/14* | (2006.01) |
| *A43B 13/14* | (2006.01) |
| *A61F 5/14* | (2006.01) |

(52) U.S. Cl.
CPC ........... *A61H 3/00* (2013.01); *A43B 7/144* (2013.01); *A43B 7/147* (2013.01); *A43B 7/1445* (2013.01); *A43B 13/145* (2013.01); *A61F 5/14* (2013.01)

(58) Field of Classification Search
CPC .......... A61H 3/00; A43B 7/144; A43B 7/147; A43B 7/1445; A43B 13/145; A61F 5/14
USPC .......... 33/6, 3 A, 3 B, 3 C, 3 R, 4, 512, 515; 601/28
See application file for complete search history.

(56) References Cited

U.S. PATENT DOCUMENTS

| | | | |
|---|---|---|---|
| 1,021,142 A | 3/1912 | Freeman | |
| 1,061,353 A | 5/1913 | Block | |
| 1,736,576 A | 11/1929 | Cable | |
| 2,096,500 A * | 10/1937 | McCahan | A43B 3/128 33/3 A |

(Continued)

FOREIGN PATENT DOCUMENTS

| | | |
|---|---|---|
| CA | 2340124 A1 | 11/2000 |
| DE | 1907894 | 1/1965 |

(Continued)

*Primary Examiner* — R. A. Smith
*Assistant Examiner* — Tania Courson
(74) *Attorney, Agent, or Firm* — Roach Brown McCarthy & Gruber, P.C.; Kevin D. McCarthy

(57) ABSTRACT

Provided are methods of treating or improving neurological conditions and/or outcomes thereof in a subject afflicted with a neurological condition. The methods include placement of a device comprising at least two calibrated, differential disturbances or protuberances under the subject's foot.

14 Claims, 13 Drawing Sheets

(56) References Cited

U.S. PATENT DOCUMENTS

| | | | |
|---|---|---|---|
| 2,133,302 A | 10/1938 | Mccormick | |
| 2,303,744 A | 12/1942 | Jacobs | |
| 2,311,925 A | 2/1943 | Boos | |
| 2,518,033 A | 8/1950 | Lucas | |
| 3,402,485 A | 9/1968 | Mcmorrow | |
| 3,526,976 A * | 9/1970 | Jacobs | A43B 5/1633 280/11.3 |
| 3,782,011 A | 1/1974 | Fisher | |
| 3,916,538 A | 11/1975 | Loseff | |
| 4,176,459 A * | 12/1979 | Perser | A43D 1/02 33/3 R |
| RE31,173 E | 3/1983 | Daswick | |
| 4,821,432 A * | 4/1989 | Reiber | A43B 7/1465 36/110 |
| 4,841,648 A | 6/1989 | Shaffer et al. | |
| 4,892,090 A | 1/1990 | Kaeser | |
| 5,014,706 A | 5/1991 | Philipp | |
| 5,188,578 A | 2/1993 | Voigt | |
| 5,337,494 A | 8/1994 | Ricker | |
| 5,400,528 A | 3/1995 | Skinner et al. | |
| 5,533,282 A | 7/1996 | Kataoka et al. | |
| 5,584,787 A | 12/1996 | Guidry | |
| 5,647,145 A | 7/1997 | Russell et al. | |
| 5,682,690 A | 11/1997 | Chang | |
| 5,848,954 A | 12/1998 | Stearns et al. | |
| 5,860,228 A * | 1/1999 | Bathum | A43C 15/162 36/127 |
| 6,019,712 A | 2/2000 | Duncan | |
| 6,063,046 A | 5/2000 | Allum | |
| 6,102,832 A | 8/2000 | Tani | |
| 6,277,057 B1 | 8/2001 | Hayden | |
| 6,283,897 B1 | 9/2001 | Patton | |
| D448,920 S | 10/2001 | Montross et al. | |
| 6,311,416 B1 * | 11/2001 | Cohen | A43B 7/00 36/115 |
| 6,349,487 B1 | 2/2002 | Hice | |
| 6,393,735 B1 | 5/2002 | Berggren | |
| 6,511,404 B2 | 1/2003 | Tu | |
| 6,519,873 B1 | 2/2003 | Buttigieg et al. | |
| 6,551,225 B1 | 4/2003 | Romero | |
| 6,557,272 B2 | 5/2003 | Pavone | A43B 1/0054 36/28 |
| 6,652,432 B2 | 11/2003 | Smith | |
| 6,692,419 B2 | 2/2004 | Chen | |
| 6,742,289 B2 | 6/2004 | Celmo | |
| 6,785,987 B2 * | 9/2004 | Bucalo | A43B 21/51 36/100 |
| 6,792,703 B2 * | 9/2004 | Cohen | A43B 7/00 36/115 |
| 6,811,523 B1 | 11/2004 | Timmer | |
| 6,880,267 B2 | 4/2005 | Smaldone et al. | |
| 6,979,287 B2 * | 12/2005 | Elbaz | A43B 5/18 36/127 |
| 7,004,895 B2 | 2/2006 | Perry et al. | |
| 7,101,330 B2 * | 9/2006 | Elbaz | A43B 5/18 482/148 |
| 7,165,343 B2 | 1/2007 | Fukui | |
| 7,373,740 B2 | 5/2008 | Lo | |
| 7,500,324 B1 * | 3/2009 | Power | A43B 13/145 36/132 |
| 7,707,751 B2 | 5/2010 | Avent et al. | |
| 8,533,980 B2 * | 9/2013 | Elbaz | A43B 7/1465 36/103 |
| 8,740,757 B1 * | 6/2014 | FioRito | A63B 22/18 36/74 |
| 8,758,207 B2 * | 6/2014 | Elbaz | A43B 5/18 36/102 |
| 8,984,770 B1 * | 3/2015 | Piontkowski | A43B 1/0054 36/102 |
| 2002/0026730 A1 | 3/2002 | Whatley | |
| 2002/0038522 A1 | 4/2002 | Houser et al. | |
| 2002/0092201 A1 | 7/2002 | Kraeuter et al. | |
| 2002/0100190 A1 | 8/2002 | Pellerin | |
| 2002/0139011 A1 | 10/2002 | Kerrigan | |
| 2002/0166258 A1 | 11/2002 | Posa | |
| 2003/0148865 A1 | 8/2003 | Handshoe | |
| 2003/0188458 A1 * | 10/2003 | Kelly | A43C 15/164 36/128 |
| 2004/0033864 A1 | 2/2004 | Elbaz et al. | |
| 2004/0033874 A1 * | 2/2004 | Elbaz | A43B 5/18 482/148 |
| 2005/0235526 A1 | 10/2005 | Kim | |
| 2006/0130372 A1 * | 6/2006 | Auger | A43C 15/14 36/134 |
| 2007/0051020 A1 | 3/2007 | Tajima et al. | |
| 2007/0079532 A1 | 4/2007 | Ramirez | |
| 2007/0193071 A1 | 8/2007 | Gilmore | |
| 2008/0134541 A1 * | 6/2008 | Bar-Haim | A61B 5/1038 36/27 |
| 2008/0229611 A1 | 9/2008 | Chiodo et al. | |
| 2008/0242518 A1 * | 10/2008 | Elbaz | A43B 5/18 482/54 |
| 2009/0172975 A1 * | 7/2009 | Keough | A43C 15/161 36/127 |
| 2009/0199429 A1 | 8/2009 | Ellis | |
| 2010/0325919 A1 | 12/2010 | Elbaz | |
| 2011/0047831 A1 * | 3/2011 | Elbaz | A43B 7/00 36/136 |
| 2011/0126422 A1 | 6/2011 | Vattes et al. | |
| 2012/0073166 A1 * | 3/2012 | Bryla | A43B 1/0081 36/132 |
| 2013/0165834 A1 * | 6/2013 | Elbaz | A61F 5/0127 602/28 |
| 2015/0150713 A1 * | 6/2015 | Ward | A61F 5/14 33/515 |

FOREIGN PATENT DOCUMENTS

| | | |
|---|---|---|
| DE | 29701013 | 3/1997 |
| DE | 29902731 | 3/2000 |
| DE | 10133863 | 2/2003 |
| EP | 925809 | 6/1999 |
| EP | 2462827 | 6/2012 |
| FR | 1128009 | 1/1957 |
| JP | 2007029700 | 2/2007 |
| KR | 20030058556 | 7/2003 |
| WO | 9620651 | 7/1996 |
| WO | 9713422 | 4/1997 |
| WO | 0067846 | 11/2000 |
| WO | 0137693 | 5/2001 |
| WO | 0237995 | 5/2002 |
| WO | 03090868 | 11/2003 |
| WO | 2004016321 | 2/2004 |
| WO | 2004043185 | 5/2004 |
| WO | 2006005139 A1 | 1/2006 |
| WO | 2006065070 A1 | 6/2006 |
| WO | 2011024162 A1 | 3/2011 |
| WO | 2012001685 | 1/2012 |

* cited by examiner

DEVICE AND METHODS OF TREATING NEUROLOGICAL DISORDERS

FIELD OF INVENTION

This invention is directed, inter alia, to device and methods for treating neurological disorders and/or symptoms related thereto and/or for improving neurological and related functions in a subject in need thereof.

BACKGROUND OF THE INVENTION

Various neurological conditions and disorders are known, which can affect various neurological related functions of subjects afflicted with such conditions. The neurological conditions impair one or more functions or parts of the neurological system, which may results in impaired functioning of a subject afflicted with such condition. For example, symptoms of neurological conditions may include cognitive, emotional, sensory and motor impairments.

Many neurological conditions are known in the art. For example, stroke or cerebrovascular accident (CVA), is a condition which commonly occurs in elderly individuals (over 65) and may be divided into two categories; ischemic CVA and hemorrhagic CVA. Ischemic CVA is caused by blockage of a blood vessel supplying blood to the brain resulting in temporary or permanent damage to the neurons in that area. The blockage of the artery can be a result of an embolus, occlusion of the artery due to a local formation of a blood clot, narrowing of the artery due to deposits (such as, for example, calcium, cholesterol, lipids and the like) in the intima and media layers of the artery walls. If the symptoms subside completely within 24 hours, the CVA is considered a transient ischemic attack (TIA). Hemorrhagic CVA- is caused by tear of the artery walls which causes bleeding into the brain resulting in both a compromised blood supply to the area of the brain supplied by the blood vessel (hence resulting in localized damage) and an increase in the intracranial pressure (hence resulting in damage to the entire brain). Any process that weakens the artery walls will increase the risk for a hemorrhagic stroke. Such processes include, for example, an aneurism, amyloid angiopathy and others.

Another neurological condition is Traumatic Brain Injury (TBI). TBI is an injury to the brain as a result of a force applied to the head which exceeds the ability of the natural protective mechanism to protect the brain. This may cause a penetrating head injury or blunt head trauma which may injure the brain. In both cases the blood supply to the brain may be compromised. Bleeding can result in an epidural hematoma, subdural hematoma, subarachnoid hematoma or bleeding within the ventricles of the brain. The type and severity of the symptoms of CVA and TBI may vary greatly ranging from death or a deep comatose state to lack of any long term symptoms. Patients who are in need of a treatment may suffer from any or a combination of the following symptoms: hemiparesis, monoparesis, increased/decreased muscle tone, reduced balancing abilities, dysmetria, loss of parts of the field of vision such as hemianopsia, aphasia (motoric or sensory), dysarthria, central pain, diminished cognitive capabilities as well as other problems.

An additional neurological condition is Anoxic Brain Damage (ABD). Anoxic brain damage is caused by lack of oxygen supply to the entire body affecting the brain. Causes can include drowning, asphyxiation, myocardial infarction leading to asystole (heart attack) or a severe arrhythmia of the heart such as ventricular fibrillation. Symptoms may affect all brain functions and include cognitive, emotional, sensory and motor impairments.

Another neurological condition is Cerebral Palsy (CP). CP usually occurs due to compromised blood supply to motor or motor related areas of the developing brain. The damage may occur during pregnancy, congenitally or up to the age of 3 years. The term Cerebral Palsy is directed to many subtypes of movement disorders, the most common of which is spastic CP. The symptoms may include the lower limbs such as in spastic diplegia, or the symptoms may involve the upper limbs as well such as in hemiplegia or hemiparesis, mixed hemiparesis (when for example one hand and the contra lateral leg are involved), quadriplegia/quadriparesis. In a minority of the cases some patients may suffer from athetoid CP or ataxic CP. The condition itself is non-progressive but since movement disorder is present from the beginning of life it may have a severe impact on the growing musculoskeletal system. CP patients may have asymmetric hands or legs (left compared to right), scoliosis, early onset of osteoarthritis and other musculoskeletal ramifications. Aside from the musculoskeletal direct and indirect effects CP patients may also suffer from disturbances of sensation, depth perception and other sight-based perceptual problems.

An additional neurological condition is Parkinson's disease (PD). Parkinson's disease is a progressive disease involving the basal ganglia network, mainly the sustantia nigra. The progressive lack of the neurotransmitter dopamine slowly affects all the functions of the basal ganglia network which include movement control, balance, cognitive functions, affect, perception (visual and cognitive) and others. The direct symptoms of the disease include tremor, rigidity (increased muscle tone) bradykinisia (slowness of movement), shuffle gait, festinating gait, freezing episodes, impaired balance and a forward flexed posture. Muscle and joint pain are common results of the above direct symptoms of the disease. As the disease progresses patients show mental decline and may develop hallucinations.

Another neurological condition is Multiple Sclerosis (MS). Multiple sclerosis (MS) is an inflammatory (autoimmune) progressive disease of the central nervous system (spinal cord and the brain). The inflammation process leads to break down of the myelin sheaths of the axons, rendering them unable to conduct neural impulses. Several subtypes have been described according to the progression of the disease: Relapsing remitting, Secondary progressive, Primary progressive and Progressive relapsing. The disease may impact all or any of the areas of the central nervous system. Symptoms may include sensory symptoms (loss of vision, proprioceptive deficits, loss of superficial sensation from various areas etc.), motor symptoms (paresis or paralysis, high muscle tone, clonus etc.), ataxia, cognitive symptoms, fatigue and pain. As the disease progresses, most patients condition becomes worse and they need support during ambulation. Supports can include braces, ankle-foot orthoses, sticks and walkers. In most cases independent ambulation becomes impossible after a while.

An additional neurological condition is Spinal Cord Injury (SCI). SCI may be cause by blunt force such as a fall off height, penetrating wounds such as gunshot wounds or surgical interventions, disc pathologies and fractures of the spinal column. SCI can cause complete destruction of the cord or any degree of partial damage to it. The degree of damage to the cord as it is expressed in the ability of the muscles to function is the basis for the most widely used classification for SCI: the American Spinal Injury Association scale, commonly known as the ASIA scale (for example, see http://www.sci-info-pages.com/levels.html). In the vast majority of the cases, the injury causes damage to both sensory and motor nerves in the spinal cord, resulting in both sensory and motor deficits. These deficits can be seen below the level of injury or at the level of injury. Patients who have suffered an injury to the cervical spine are likely to have symptoms which include the upper and lower extremities, a condition called quadriplegia or quadriparesis. Patients who have suffered an injury to the thoracic spine or lower will have symptoms which include the lower extremities, a condition called paraplegia or paraparesis. Some of the SCI patients develop central pain in the hypoaesthetic/anaesthetic areas of the body. This type of pain is caused by the injury to the neural circuitry in the CNS. Patients with an injury rated A or B on the ASIA scale are unable to walk. Most of the patients who score C to E on the ASIA scale are able to walk but may need assistance in the form of braces, artificial foot orthoses, sticks or walkers. All SCI patients have a high probability of developing pressure sores, deformities due to increased muscle tone and muscle contractures, osteoarthritis and joint damages due to gait deviations as well as a multitude of visceral and vascular problems. All of these are secondary to the SCI.

Another neurological condition is Charcot-Marry-Tooth (CMT). CMT is a genetic defect in the axons and myelin sheaths of the peripheral nerves. In most cases the longer nerves are most affected and most patients have more severe symptoms in their feet and hands. Motor and sensory (touch) nerves are affected. The first symptom to appear is often drop foot. The symptoms usually appear in the late teen years and in the vast majority of cases progress slowly or even stop progressing within a few years. Due to the wasting of the muscles the joints of the feet often become deformed and weight bearing becomes painful. In order to support the deformed structures and the weakened muscles braces and insoles are widely used.

An additional neurological condition is Guillain-Barré syndrome (GBS). GBS is neurological disease which is caused by an autoimmune reaction to a virus. The autoimmune reaction attacks the peripheral nervous system which leads, in most types of the disease, to a progressive loss of neural functions advancing from distal to proximal. The immune system attacks the myelin sheaths which surround the nerves and enable proper conduction of neural signals along the axon. Some cases develop a paralysis of the respiratory muscles which may render the disease potentially fatal. Such cases require mechanical ventilation. Known treatment includes plasmapharesis or the administration of intravenous immunoglubulins. These treatments must be given within the first two weeks following the initial symptoms and are both aimed at reducing the autoimmune reaction in order to minimize nerve damage. The course of the disease is usually self-limiting and most (about 80%) patients recover completely within a year. Some cases continue to exhibit signs of neural damage.

An additional neurological condition is Poliomyelitis. Poliomyelitis is a viral disease which in the vast majority of cases affects the digestive system and the blood (viremia). In a small percentage of cases the virus attacks the motor neurons in the spinal cord, brainstem and motor cortex. Since the discovery of the vaccine in the 1950's, polio epidemics are virtually nonexistent in the western world. In third world countries some new cases may appear, most commonly afflicting young children. Some of the patients which exhibit signs of paralysis recover completely while others continue to have varying degrees of paresis or paralysis. Since the disease is usually contracted at a young age the prolonged paresis or paralysis leads to severe disfigurement of the affected limbs. The paralytic limbs become smaller in comparison to the healthy limb and in many cases also rotated abnormally. The weakened muscular support for the joints leads to uneven loads and unnatural forces acting on the joints and therefore joint degeneration. Many of the patients require the use of braces and artificial supports in an attempt to minimize the effects on the joints. Many of the patients can develop post-polio syndrome. The symptoms include new muscle weakness and extreme fatigue. Since over activity of the motor neurons has been found to be a contributing factor to the development of post-polio syndrome, polio patients are encouraged not to be overly active.

There is a need in the art for devices and methods that can treat such neurological conditions, improve neurological and muscular control and/or improve/reduce the outcomes thereof, in particular, outcomes related to the sensory system, the motor system and/or the movement of subjects afflicted with such conditions.

SUMMARY OF THE INVENTION

According to some embodiments, the present invention provides for methods for treating a subject afflicted with a neurological condition by improving sensory, motor and/or movement parameters of the subject, the methods comprising improving/restoring neurological control and/or neurological function to the subject. In some embodiments, the subject is afflicted with a neurological condition which is affecting the subjects' gait and the methods of the invention can improve the gait parameters of the subject. In some embodiments, the methods improve and/or restore neuromuscular control to the subject.

In some embodiments, the methods disclosed herein are based on the unexpected finding that by using the methods and device disclosed herein, various sensory, motoric and/or movement related conditions attributed to the neurological disorders/conditions can be treated, i.e. improved and/or cured. In some embodiments, the methods disclosed herein are based on the unexpected finding that by using the methods and device disclosed herein, a sensory feedback and improvement in neuro-muscular control is achieved, thereby, various sensory, motoric and/or movement related conditions attributed to the neurological disorders/conditions can be treated. In some embodiments, sensory feedback and improvement in neuro-muscular control is achieved in a subject in need thereof, by calibrating and adjusting the device disclosed herein, for instance, by adjusting/calibrating it's perturbation. In further embodiments, by changing the center of pressure (COP) with which the foot contacts the ground, various sensory, motoric and/or movement related conditions attributed to the neurological disorders/conditions can be treated. i.e. improved and/or cured. In another embodiment, changing the center of pressure (COP) with which the foot contacts the ground is executed through calibrating the device (footwear units) of the invention. In another embodiment, COP is changed or altered via a perturbation induced by a protuberance as disclosed herein, wherein the protuberance may be calibrated as further detailed below. In another embodiment, a device of the invention alters COP thus changing the movement pattern of a lower limb. In another embodiment, the methods of the invention provide a controlled change in movement pattern and concomitantly improve gait parameters and are able to aid in avoiding damage, injury, trauma, or a combination thereof (such as but not limited to: falls, damaging gait, damaging lower limb neuromuscular control or activity) to the subject using the device, thus efficiently enabling the accomplishment of the methods provided herein.

In one embodiment, the present invention provides a method of treating a subject afflicted with a neurological condition comprising the steps of: (a) securing a device to a subject's foot, whereby the device comprises a foot securing mean, a support member operably attached to said securing mean, and a moveable/relocatable anterior protuberance and a moveable/relocatable posterior protuberance, wherein the anterior protuberance and the posterior protuberance are ground engaging; (b) calibrating the posterior protuberance and the anterior protuberance to: a balanced position, wherein the balanced position comprises a position whereby the device provides a reduced inversion, a reduced eversion, or both to the subject's foot during the stance phases; and (c) fixing said posterior protuberance and the anterior protuberance to the support member. In some embodiments, the calibrating may further comprise balancing timing of heel rise.

In another embodiment, the present invention provides a method of improving gait in a subject afflicted with a neurological condition, comprising the steps of: (a) securing a device to a subject's foot, whereby the device comprises a foot securing mean, a support member operably attached to said securing mean, and a moveable/relocatable anterior protuberance and a moveable/relocatable posterior protuberance, wherein the anterior protuberance and the posterior protuberance are ground engaging; (b) calibrating the posterior protuberance and the anterior protuberance to: (1) a balanced position, wherein the balanced position comprises a position whereby the device provides a reduced inversion, a reduced eversion, or both to the subject's foot during the stance phases; and optionally (2) balanced timing of heel rise; and (c) fixing said posterior protuberance and the anterior protuberance to the support member.

In some embodiments, the present invention provides a method of improving/restoring neuro-muscular control and/or neural sensory and motor function of a subject having a neurological disorder, the method comprising the steps of: (a) securing a device to a subject's foot, whereby the device comprises a foot securing mean, a support member operably attached to said securing mean, and a moveable/relocatable anterior protuberance and a moveable/relocatable posterior protuberance, wherein the anterior protuberance and the posterior protuberance are ground engaging; (b) calibrating the posterior protuberance and the anterior protuberance to: (1) a balanced position, wherein the balanced position comprises a position whereby the device provides a reduced inversion, a reduced eversion, or both to the subject's foot during the stance phases; and optionally, (2) balanced timing of heel rise; and (c) fixing said posterior protuberance and the anterior protuberance to the support member.

According to some embodiments, there is provided a method of treating a subject suffering from neurological disorder comprising the steps of: (a) securing a device to a subject's foot, whereby said device comprises a foot securing mean, a support member operably attached to said securing mean, and a moveable/relocatable anterior protuberance and a moveable/relocatable posterior protuberance, said anterior protuberance and said posterior protuberance are ground engaging; (b) calibrating said posterior protuberance and said anterior protuberance to: a balanced position, said balanced position comprises a position whereby said device provides a reduced inversion, a reduced eversion, or both to said subject's foot during stance phases; and (c) fixing said posterior protuberance and said anterior protuberance to said support member; thereby treating a subject suffering from a neurological disorder; wherein the subject is capable of walking.

In some embodiments, the calibrating comprises adjusting: (a) a resilience of said anterior protuberance, said posterior protuberance, or a combination thereof; (b) a hardness of said anterior protuberance, said posterior protuberance, or a combination thereof; (c) an elasticity of said anterior protuberance, said posterior protuberance, or a combination thereof; (d) or any combination of (a), (b), and (c). In further embodiments, calibrating further comprises balancing timing of heel rise. According to additional embodiments, calibrating comprises adjusting: (a) a height of said anterior protuberance, said posterior protuberance, or a combination thereof; (b) a convexity of said anterior protuberance, said posterior protuberance, or a combination thereof; (c) a weight of said anterior protuberance, said posterior protuberance, or a combination thereof (d) and a combination of (a), (b), and (c).

According to some embodiments, the balanced position further comprises a position whereby a reduced valgus, varus, dorsal or plantar torque about the ankle is exerted by said device on said subject's foot.

According to additional embodiments, the posterior protuberance is a bulbous protuberance, said anterior protuberance is a bulbous protuberance, or both said posterior protuberance and said anterior protuberance are bulbous protuberances.

In further embodiments, the posterior protuberance and the anterior protuberance are moveably mounted to said support member. In some embodiments, the posterior protuberance is movable within a calcaneus support portion of said support member. In further embodiments, the anterior protuberance is movable within phalanges or metatarsals support portion of said support member. In some embodiments, the anterior protuberance, said posterior protuberance, or their combination comprise a cross-section with a shape of a conic section, said conic section comprising at least one of a circle, ellipse, parabola and hyperbola. In another embodiment, the anterior protuberance is shaped differently from said posterior protuberance.

According to further embodiments, the neurological disorder is selected from: stroke, cerebrovascular accident (CVA), ischemic CVA, hemorrhagic CVA, Traumatic Brain Injury (TBI), Anoxic Brain Damage (ABD), Cerebral Palsy (CP), Parkinson's disease (PD), Multiple Sclerosis (MS), Spinal Cord Injury (SCI), Charcot-Marry-Tooth (CMT), Guillain-Barré syndrome (GBS) and Poliomyelitis.

In some embodiments, the improvement in neurological control comprises improvement in gait parameters of the subject. In some embodiments, the gait parameters are selected from: velocity, step length, single limb support, stability and combinations thereof.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

This invention provides, in some embodiments, a method of treating a subject suffering from a neurological disorder/condition comprising the steps of: (a) securing a device to a subject's foot, whereby the device comprises a foot securing mean, a support member operably attached to said securing mean, and a moveable/relocatable anterior protuberance and a moveable/relocatable posterior protuberance, wherein the anterior protuberance and the posterior protuberance are ground engaging; (b) calibrating the posterior protuberance and the anterior protuberance to: a balanced position, wherein the balanced position comprises a position whereby the device provides a reduced inversion, a reduced eversion, or both to the subject's foot during the stance phases; and (c) fixing said posterior protuberance and the anterior protuberance to the support member.

In another embodiment, the present invention provides a method of improving gait and/or balance in a subject suffering from a neurological disorder/condition comprising the steps of: (a) securing a device to a subject's foot, whereby the device comprises a foot securing mean, a support member operably attached to said securing mean, and a moveable/relocatable anterior protuberance and a moveable/relocatable posterior protuberance, wherein the anterior protuberance and the posterior protuberance are ground engaging; (b) calibrating the posterior protuberance and the anterior protuberance to: a balanced position, wherein the balanced position comprises a position whereby the device provides a reduced inversion, a reduced eversion, or both to the subject's foot during the stance phases; and (c) fixing said posterior protuberance and the anterior protuberance to the support member. In another embodiment, securing is fastening or adapting.

In another embodiment, stance phases comprise initial contact of foot with ground, loading bodyweight onto the stance leg (loading response), mid-stance, heel off, and push off.

Figure 1:
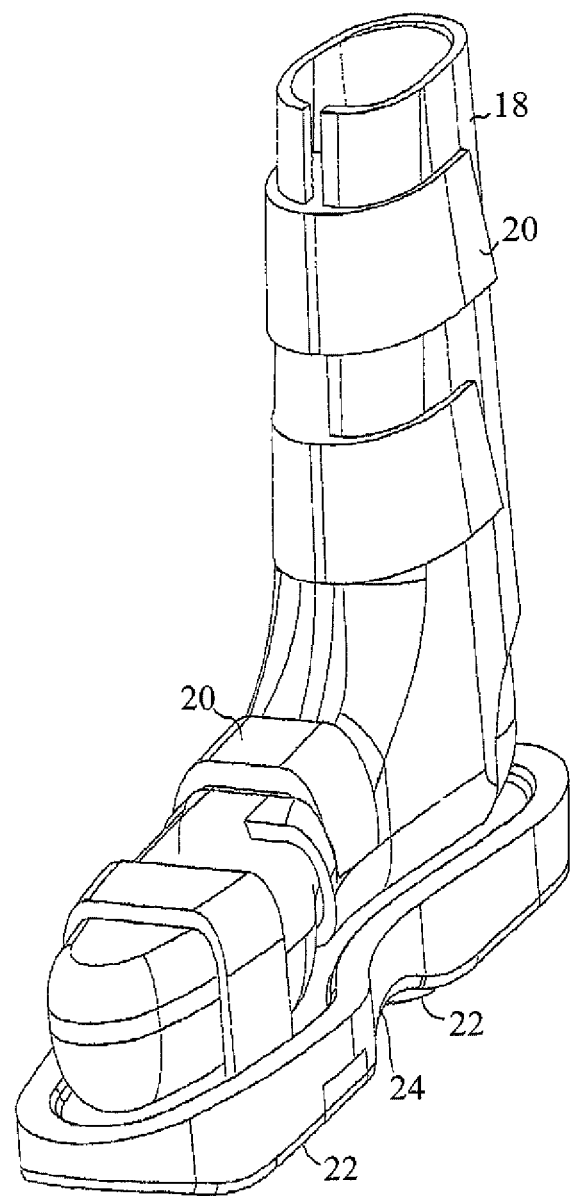
FIG. 1 is a simplified pictorial illustration of footwear constructed and operative in accordance with an embodiment of the present invention.

In another embodiment, balancing timing of heel rise comprises correcting instances wherein the heel is pulled off the ground earlier than normal-early-heel rise. In another embodiment, the typical pattern is a whipping motion upwards and medial. In another embodiment, correction comprises lifting a posterior protuberance thus bringing an ankle towards a plantar flexed position. This is done, in some embodiments, by the insertion of, for example, but not limited to, a 0.5-8 mm spacer (spacer being a mean for introducing/creating differential height or differential amount of protrusion) between the protuberance and the lower surface (element 24 in FIG. 1 or 2) or outsole, thus bringing the ankle towards a plantar flexed position. In another embodiment, lifting a protuberance is increasing the height of a protuberance. In another embodiment, lifting a protuberance is increasing the convexity of a protuberance, thereby increasing its height.

In another embodiment, a protuberance of the invention comprises low convexity designated as convexity A, low-medium convexity designated as convexity B, medium convexity designated as convexity C, medium-high convexity designated as convexity D, or high convexity designated as convexity D. In another embodiment, a protuberance of the invention has a base diameter of 55-120 mm. In another embodiment, a protuberance of the invention has a base diameter of 75-100 mm.

In another embodiment, convexity A protuberance has a base diameter of 70-100 mm and a height, which is a perpendicular line connecting the highest point and the base, of 10-13 mm. In another embodiment, convexity B protuberance has a base diameter of 70-100 mm and a height, which is a perpendicular line connecting the highest point and the base, of 14-16 mm. In another embodiment, convexity C protuberance has a base diameter of 70-100 mm and a height, which is a perpendicular line connecting the highest point and the base, of 16-18 mm. In another embodiment, convexity D protuberance has a base diameter of 70-100 mm and a height, which is a perpendicular line connecting the highest point and the base, of 19-22 mm. In another embodiment, the highest point is ground engaging.

In some embodiments, the calibration further comprises balancing timing of heel rise. In another embodiment, balancing timing of heel rise comprises correcting instances termed late-heel rise. In another embodiment, late-heel rise is observed as a wobbling medial and lateral rocking motion of the foot. In another embodiment, correction comprises lifting an anterior protuberance thus bringing an ankle towards a slightly more dorsi-flexed position. This is done, in some embodiments, by the insertion of a 0.5-8 mm spacer between the protuberance and the lower surface (element 24 in FIG. 1 or 2) or outsole, thus bringing the ankle towards a slightly more dorsi-flexed position.

According to some embodiments, the methods disclosed herein for the treatment of neurological conditions or symptoms related thereto, surprisingly and unexpectedly provide beneficial effects to a subject in need thereof. For example, the methods disclosed herein, can improve balance of a subject afflicted with a neurological condition via improved muscle coordination, motor learning, normalized gait pattern, desired alignment of the joints in the lower limb and low back. For example, the methods disclosed herein can improve dysmetria of a subject having a neurological condition, via mechanism of brain plasticity, motor learning, improved and more precise proprioception and interpretation of proprioceptive and vestibular input as well as improved muscle coordination and/or neurological coordination of a subject afflicted with a neurological condition. For example, the methods disclosed herein can reduce muscle tone of a subject having a neurological condition, via desired alignment of the joints in the lower limb and low back, reduced muscle bracing as a response to the innate perturbation of a subject afflicted with a neurological condition. For example, the methods disclosed herein can reduce the energy cost of gait of a subject afflicted with a neurological condition, via improved muscle coordination, motor learning, normalized gait pattern, desired alignment of the joints in the lower limb and low back in a subject afflicted with a neurological condition. For example, the methods disclosed herein can increase neuronal sprouting of a subject afflicted with a neurological condition, via repetitive stimulation of a desired movement pattern (central nervous system) and repeated muscular activation (peripheral nervous system). For example, the methods disclosed herein can increase neurological system plasticity of a subject afflicted with a neurological condition. For example, the methods disclosed herein can prevent joint pain, deformity and contractures (both in the joint and various muscles) of a subject having a neurological disorder, via redistribution of loads in the joints, improved muscular activity and reduced muscle tone. For example, the methods disclosed herein can prevent falls of a subject afflicted with a neurological condition, via improved balance, reduced muscle tone, improved dysmetria, improved alignment and posture.

In some embodiments, the methods disclosed herein are directed to methods of improving the control over gait function. In some embodiments, the methods disclosed herein are based on the unexpected discovery that by changing the center of pressure (COP) with which the foot contacts the ground, various gait related conditions caused by neurological disorders can be treated, improved and/or completely cured. In another embodiment, changing the center of pressure (COP) with which the foot contacts the ground is executed through calibrating the device (footwear) of the invention. In another embodiment, COP is changed or altered via a perturbation induced by a protuberance as disclosed herein. In another embodiment, a device of the invention alters COP thus changing the movement pattern of a lower limb. In another embodiment, the methods of the invention provide a controlled change in movement pattern and concomitantly avoiding damage, injury, trauma, or a combination thereof (such as but not limited to: falls, damaging gait, damaging lower limb neuromuscular control or activity) to the subject using the device, thus efficiently enabling the accomplishment of the methods provided herein.

In another embodiment, methods of the present invention unexpectedly provide exercises to strengthen various muscles and improve neuromuscular control. In some embodiments, the exercises comprise standing. In another embodiment, methods of the present invention are suitable to any person that can walk to any extent. In other words, methods of the present invention are suitable to any person suffering from or afflicted with a neurological condition/disorder, which still has the ability to walk. In some embodiments, methods of the present invention are suitable to a person that can stand.

In some embodiments, the device of the invention may be used in the methods disclosed herein due to the ability of the device to change the foots' point of contact with the ground, thereby altering the forces and moments acting on the entire leg (and entire body) in any weight bearing activity. Weight bearing activities are activities where the weight of the body is placed on the feet, such as walking, standing, getting up from a chair, and the like. In some embodiments, the device has an inherent perturbation which integrates a controlled amount of instability into any weight bearing activity. This increases the demand on both the neural and the muscular system with regards to the demand placed upon them to control movement whilst maintaining the body's stability as a whole and the stability of the individual joints. The increased demand promotes motor learning thereby enhancing the patient's ability to perform tasks with and without the device. Specifically, the calibration of the anterior protuberance and/or the posterior protuberance, including change of position of the protuberance in relation to the sole of the device, change of height of the anterior protuberance in relation to the height of the posterior protuberance, or changing the height of both anterior and posterior protuberances of one leg in relation to the height of both anterior and posterior protuberances of the other leg, change of the resilience of the protuberances, changing the weight of the protuberances can results in a controlled effect on the forces and moments and the muscular activity.

In another embodiment, the methods of the invention provide that the subject wearing the device performs (daily) activities such as, for example, but not limited to: walking, standing, cooking or getting up from a chair with the device worn on both feet. In some embodiments, the device comprises 2 units of footwear: one for the left foot and one for the right foot. In another embodiment, each unit of the device comprises at least two protuberances wherein only the protuberances are ground engaging during activities such: walking, standing, cooking or getting up from a chair with the device worn on both feet. In another embodiment, each unit of the device comprises at least two protuberances wherein predominantly the protuberances are ground engaging during activities such: walking, standing, cooking or getting up from a chair with the device worn on both feet.

In another embodiment, predominantly is over 50% of the ground engaging period. In another embodiment, predominantly is over 60% of the ground engaging period. In another embodiment, predominantly is over 70% of the ground engaging period. In another embodiment, predominantly is over 80% of the ground engaging period. In another embodiment, predominantly is over 90% of the ground engaging period. In another embodiment, predominantly is over 95% of the ground engaging period.

In another embodiment, ground engaging period is the period in percent of the gait cycle wherein part of the footwear is in contact with a ground surface. In another embodiment, ground engaging period is the period in percent of the gait cycle wherein part of the footwear is in contact with a ground surface during gait and/or stance.

Target Populations

In some embodiments, the subject to be treated is a human subject. In some embodiments, a subject in need thereof is a subject suffering from or afflicted with a neurological condition or disorder, but which still has at least an ability to walk. In some embodiments, the neurological condition or disorder affects the sensory system of the subject, and/or the motor system of the subject. In some embodiments, the neurological condition or disorder affects the gait of the subject. In some embodiments, the subject is capable of walking without assistance. In some embodiments, the subject is capable of walking with the assistance of various walking aids, such as, for example, cane, crutches, walker, and the like. In some embodiments, the subject has both functional feet and legs, which enable walking. In some embodiments, one or both feet or legs are prosthesis (i.e. artificial). In some embodiment, the prosthesis allows the subject to walk.

As referred to herein, the term "walking" is directed to spatial movement of a two legged subject from one location to another by lifting and setting down each foot in turn. In another embodiment, walking is gait.

As referred to herein, the terms "neurological condition" and "neurological disorder" may interchangeably be used. The terms are directed to a condition which affects the neurological system of a subject. The neurological condition may be caused by a disease (for example, a genetic disease, an acquired disease, an autoimmune disease), an injury, infection, and the like, which may affect the neurological system of the subject. In some embodiments, the neurological condition results in gait impairment. In some embodiments, the neurological condition affects the sensory system of the subject, the motoric system of the subject, the neuromuscular system of the subject, the peripheral nervous system, the proprioceptive system of the subject, the cognitive system of the subject, the balancing abilities of the subject or combinations thereof.

In some embodiments, the neurological condition may be at different stages of progression, and may be selected from, but not limited to: stroke, cerebrovascular accident (CVA), ischemic CVA, hemorrhagic CVA, Traumatic Brain Injury (TBI), Anoxic Brain Damage (ABD), Cerebral Palsy (CP), Parkinson's disease (PD), Multiple Sclerosis (MS), Spinal Cord Injury (SCI), Charcot-Marry-Tooth (CMT), Guillain-Barré syndrome (GBS), Poliomyelitis and combinations thereof. Each possibility is a separate embodiment of the invention. In some embodiments, the neurological condition may include pathologies of the peripheral nervous system. In some embodiments, pathologies of the peripheral nervous system are lacerations of peripheral nerves leading to sensory or motor deficits. In some embodiments, pathologies of the peripheral nervous system are peripheral neuropathies such as, for example, but not limited to: diabetic neuropathy, vasculitis, sarcoidosis, vitamin deficiency, and the like. In some embodiments, pathologies of the peripheral nervous system are compartment syndrome. In some embodiments, pathologies of the peripheral nervous system are nerve compression or neurotmesis, axonopraxia or axonotmesis. In another embodiment, pathologies of the peripheral nervous system are nerve entrapments such as, but not limited to tarsal tunnel syndrome or entrapment of the common peroneal nerve. In some embodiments, pathologies of the peripheral nervous system are injuries to the lumbar plexus, pelvic plexus or brachial plexus. In some embodiments pathologies of the peripheral nervous system are injuries or pathologies concerning nerve roots, such as, for example, but not limited to: nerve root compression and nerve root irritation. In some embodiments, the neurological condition may be caused as a results of an infection (viral, fungal, bacterial), such as, for example, polio disease.

In another embodiment, a subject in need thereof is a subject suffering from a stroke. In another embodiment, a subject in need thereof is a subject suffering from an ischemic cerebrovascular accident (CVA). In another embodiment, a subject in need thereof is a subject suffering from a hemorrhagic cerebrovascular accident (CVA). In another embodiment, a subject in need thereof is a subject suffering from a Traumatic Brain Injury (TBI), In another embodiments, a subject in need there of is a subject suffering from Anoxic Brain Damage (ABD). In another embodiment, a subject in need thereof is a subject suffering from Cerebral Palsy (CP). In another embodiment, a subject in need thereof is a subject suffering from Parkinson's disease (PD). In another embodiment, a subject in need thereof is a subject suffering from Multiple Sclerosis (MS). In another embodiment, a subject in need thereof is a subject suffering from Spinal Cord Injury (SCI). In another embodiment, a subject in need thereof is a subject suffering from Charcot-Marry-Tooth (CMT). In another embodiment, a subject in need thereof is a subject suffering from Guillain-Barré syndrome (GBS). In another embodiment, a subject in need thereof is a subject suffering from Poliomyelitis. In another embodiment, a subject in need thereof is a subject suffering from polio. In another embodiment, a subject in need thereof is a subject suffering from pathology of the peripheral nervous system.

In some exemplary embodiments, when the neurological condition is Guillain-Barré syndrome (GBS), the methods of the present invention can be practiced during the sub-acute and chronic stages of the disease and in subjects, in which the damage of the condition is to the motor system, (for example, resulting in muscle weakness).

In another embodiment, the methods described herein are preformed by calibration of an anterior protuberance, a posterior protuberance or both. In another embodiment, the methods described herein involve wearing the device and performing daily activities with it, such as walking, household chores etc.

In another embodiment, the posterior protuberance, the anterior protuberance or both are calibrated in both the left and the right footwear to a position in which reduced inversion and/or reduced eversion of the ankle is achieved. In another embodiment, the posterior protuberance, the anterior protuberance or both are calibrated in both the left and the right footwear to a position in which reduced inversion and/or reduced eversion of the foot is achieved. In another embodiment, the posterior protuberance, the anterior protuberance or both are then fixed and the subject is given a treatment plan which details the amount of time the device should be worn per day. The treatment plan also details how much time out of the total wearing time should be spent in weight bearing (i.e. on ones feet).

In another embodiment, calibrating a protuberance comprises calibrating convexity, calibrating height, calibrating weight, calibrating position, calibrating base diameter, or any combination thereof. In another embodiment, the methods as described herein reduce pain of the subject. In another embodiment, the methods as described herein enhance the control over neuromuscular activity. In another embodiments, the methods as described herein improve gait parameters of the subject.

In another embodiment, placement (being the function of the initial step of positioning a protuberance according to the invention) and calibration of a protuberance comprises the induction of a differential interference during gait or walking. In another embodiment, the term "interference" comprises disturbance, interruption, interposition, perturbation, obstruction, or any combination thereof. In another embodiment, the ability to fine-tune an induced interference under a foot of a subject enables reducing or minimizing inversion and/or eversion as described herein. In another embodiment the balanced position comprises a position whereby the device provides a reduced inversion, a reduced eversion, or both to the subject's feet during the stance phases.

In another embodiment, provided herein that the posterior protuberance is a bulbous protuberance. In another embodiment, provided herein that the anterior protuberance is a bulbous protuberance. In another embodiment, provided herein that both the posterior (P) protuberance and the anterior (A) protuberance are bulbous protuberances.

Treating

In some embodiments, the methods as described herein involve exercise with the device as described herein. In another embodiment, exercise is walking, running, dancing, jumping or any other form of gait movement. In another embodiment, treating is curing or improving the indication provided herein or symptoms related thereto. In some embodiments, treating is improving balance symmetry. In some embodiments, treating is reducing or completely eliminating pain felt by a subject suffering from a neurological condition. In some embodiments, treating is improving the overall gait parameters of a subject suffering from a neurological condition. In some embodiments, treating is improving the gait of the subject with respect to energy cost of gait. In some embodiments, treating is improving the stability of the subject. In some embodiments, treating is improving the velocity of the subject. In some embodiments, treating is improving the step length of the subject. In some embodiments, treating is improving the single limb support of the subject. In some embodiments, treating is improving muscle strength of the subject. In some embodiments, treating is improving muscle timing and coordination. In some embodiments, treating is reducing muscle tone of the subject. In some embodiments, treating is increasing muscle tone of the subject. In some embodiments, treating is improving load distribution in the various joints of the subject. In some embodiments, treating is improving balance of the subject. In some embodiments, treating is Improving dysmetria of the subject. In some embodiments, treating is increasing neuronal sprouting (wherein neuronal sprouting is the process of growth in a damaged but still viable nerve cell (neuron), which can takes place in the peripheral or central nervous systems) of the subject. In some embodiments, treating is increasing the impact of brain plasticity. In some embodiments, treating is preventing joint pain, deformity and contractures which are often the sequelae of neurological conditions. In some embodiments, treating is improving overall neuromuscular control of the subject. In another embodiment, treating is a process wherein the subject's disease or condition is ameliorated, or the symptoms related thereto are reduced or eliminated.

In another embodiment, the methods as described herein further comprises a combination treatment comprising the use of the device as described herein and a proper additional treatment that may include, for example, medication, surgery or any other medical and/or rehabilitation interventions. In another embodiment, one of skill in the art will readily diagnose and prescribe the proper medication, surgery or other medical and rehabilitation interventions to a subject suffering from a disease or a condition such as described herein.

In another embodiment, the outcome of treatment as provided herein is apparent immediately after the initial use of the device as described herein. In some embodiments, the outcome is apparent after initial calibration. In another embodiment, the outcome of treatment as provided herein is apparent after 10-1000000 meters of walking with the device as described herein. In another embodiment, the outcome of treatment as provided herein is apparent after 50-100000 meters of walking with the device as described herein. In another embodiment, the outcome of treatment as provided herein is apparent after 500-100000 meters of walking with the device as described herein. In another embodiment, the outcome of treatment as provided herein is apparent after 500-5000 meters of walking with the device as described herein. In another embodiment, the outcome of treatment as provided herein is apparent after 500-3000 meters of walking with the device as described herein.

In another embodiment, a device as disclosed herein has an immediate effect with regard to treating or treatment of a condition, disease, a pathology, and/or pain as provided herein. In another embodiment, short term immediate effect is apparent after walking with the device for 1-5 days. In another embodiment, short term immediate effect is apparent after walking with the device for 30-600 minutes. In another embodiment, short term immediate effect is apparent after walking with the device for 1-10 hours (hrs). In another embodiment, short term immediate effect is apparent after walking with the device for 5-1000 hours (hrs). In another embodiment, short term immediate effect is apparent after walking with the device for 12-96 hours (hrs). In another embodiment, short term immediate effect is apparent after walking with the device for 1-10 days. In another embodiment, short term immediate effect is apparent after walking with the device for 7-21 days. In another embodiment, short term immediate effect is apparent walking with the device for 5-30 days.

In another embodiment, the effect is apparent after walking with the device for 1-2 months. In another embodiment, the effect is apparent after walking with the device for 1-24 months. In another embodiment, the effect is apparent after walking with the device for 2-6 months. In another embodiment, the effect is apparent after walking with the device for 4-10 months. In another embodiment, the effect is apparent after walking with the device for 6-48 months. In another embodiment, the effect is apparent in after walking with the device for 12-24 months. In another embodiment, the effect is apparent after walking with the device for 10-30 months.

In another embodiment, a device as described herein is calibrated and prescribed to a subject according to the subject's physical condition and/or additional parameters, such as, for example, according to the subject's GAIT parameters, according to subject's symptoms, and the like. In another embodiment, a device as described herein is calibrated and prescribed to a subject according to the subject's medical condition. In another embodiment, a device as described herein is calibrated and prescribed to a subject according to the subject's medical history. In another embodiment, calibrating the device includes changing the location, convexity, resilience, height, size, weight or any combination thereof of the anterior protuberance. In another embodiment calibrating the device includes changing the location, convexity, resilience, height, size, weight or any combination thereof of the posterior protuberance. In another embodiment calibrating the device includes changing the location, convexity, resilience, height, size, weight or any combination thereof of both the anterior and the posterior protuberances. In another embodiment, prescription includes directions of how to use the device. In another embodiment, prescription includes intensity of use, daily use, or daily distance directions.

In another embodiment, any prescription as described herein comprises increase in daily usage time as the subject's gait improves. In another embodiment, any prescription as described herein comprises increase in daily usage time as subject's pain decreases. In another embodiment, any prescription as described herein comprises increase in daily usage time as subject's disease or condition as described herein, improves. In another embodiment, a prescription as described herein further comprises medicating or otherwise treating the subject according to his or hers medical condition.

In another embodiment, a prescription as described herein further comprises adjustments of the device as subject's lower limb muscles are tuned or are off balance. In another embodiment, adjustments of the device comprise calibrating or positioning a protuberance as described herein.

The Device

In another embodiment, the device is secured to a subject's foot directly. In another embodiment, the term "secured to a subject's foot" comprises securing the device to any footwear such as but not limited to shoes, boots, etc that are secured to a subject's foot. In another embodiment, a foot securing means secures the device such as footwear as shown in the figures to a subject's foot. In another embodiment, various different foot securing means can be used. In another embodiment, a foot securing mean comprises a plurality of securing means. In another embodiment, a foot securing mean is a lace. In another embodiment, a foot securing mean comprises a Velcro fastener. In another embodiment, a foot securing mean comprises securing straps. In another embodiment, reference is made to FIGS. 1-4, which illustrate footwear 10 constructed and operative in accordance with an embodiment of the present invention.

In another embodiment, the device is footwear comprising a shoe structure which includes at least two calibrated, disturbances in the form of protuberances under the patient's feet. In another embodiment, the shoe structure serves as a platform for placing at least two calibrated, differential or identical disturbances or protuberances under the patient's feet.

In another embodiment, the upper part of the shoe structure serves as fastening or securing means/platform, while the sole is a platform for placing at least two calibrated, differential disturbances or protuberances under the patient's foot. In another embodiment, the outsole is a platform for placing at least two calibrated, differential or identical disturbances or protuberances under the patient's foot.

In another embodiment, a support member is operably attached to the securing mean. In another embodiment, operably attached comprises sufficient attachment between the securing mean and the support member. In another embodiment, a support member comprises the sole. In another embodiment, a support member comprises the inner sole. In another embodiment, a support member comprises the outer sole. In another embodiment, a support member comprises the middle sole. In another embodiment, a support member comprises the upper (the part of the shoe that is on top of the foot). In another embodiment, the upper is operably attached to the securing mean (such as but not limited to laces). In another embodiment, the upper comprises straps or totally enclosing the foot. In another embodiment, the upper comprises straps that function as securing means (such as sandals).

In another embodiment, a device such as footwear 10 is supplied as one or more pairs of shoe-like devices, or alternatively, as just one of the shoe-like devices. In another embodiment, footwear 10 comprises a support member 12 having a periphery in a shape of a shoe sole comprising an upper surface 14. In the illustrated embodiment, the upper surface 14 is indented with a peripheral ridge 16, but it is appreciated that other configurations of upper surface 14 are within the scope of the invention. In another embodiment, footwear 10 is attached to a foot of a user by means of a boot 18 and/or fasteners 20, such as but not limited to, VELCRO straps, buckles, shoe laces, and the like. In another embodiment, footwear 10 is attached to a foot of a user by means of a shoe. In another embodiment, a shoe comprises a platform of a sneaker. In another embodiment, the term sneaker comprises a boot. In another embodiment, the term sneaker comprises a walking boot. In another embodiment, a shoe comprises a platform of a running shoe. In another embodiment, a shoe comprises a platform of an elegant shoe. In another embodiment, a shoe comprises a platform of a walking shoe or boot.

In another embodiment, a device such as but not limited to boot 18 is fashioned for attachment to the user's foot with or without fasteners 20. In another embodiment, fasteners 20 are used as foot securing means to attach footwear 10 to the user's foot without boot 18.

Protuberances

In another embodiment, the invention provides that the device such as footwear 10 comprises protuberances in a fixed position. In another embodiment, the invention provides that the device such as footwear 10 comprises protuberances having any shape known to one of skill in the art. In another embodiment, the invention provides that the device comprises at least two bulbous protuberances. In another embodiment, a protuberance is symmetrical. In another embodiment, a protuberance is asymmetrical In another embodiment, a protuberance comprises a shape of a: polygon, decagon, digon, dodecagon, nonagon, henagon hendecagon, heptagon, hexadecagon, hexagon icosagon, octagon, pentagon, triangle, Penrose tile, trapezium, isosceles, trapezium undecagon, quadrilateral, Lozenge, rhomboid, rectangle, square, rhombus, trapezoid, polydrafter, arbelos, circle, disc, circle, excircle, crescent, dome, ellipse, lune, oval, sphere, asteroid, or deltoid.

In another embodiment, each protuberance 22 has a curved outer contour 26. In another embodiment, each protuberance has a different curved outer contour. In another embodiment, each protuberance 22 has a convexity.

In another embodiment, a protuberance comprises a dome shape. In another embodiment, a protuberance as described herein comprises a dome shape which further comprises multiple different convexities. In another embodiment, each protuberance 22 comprises a different convexity. In another embodiment, each protuberance 22 comprises a different set of convexities. The cross-section of the contour 26, that is, either the cross-section taken with respect to a longitudinal axis 28 (FIG. 4) of support member 12 (corresponding to the shape seen in FIG. 2) or the cross-section taken with respect to a latitudinal axis 30 (FIG. 4) of support member 12 (corresponding to the shape seen in FIG. 3), or any other cross-section, may have any curvilinear shape.

In another embodiment, the contours 26 may have the shape of a conic section, that is, the shape of a circle, ellipse, parabola or hyperbola. The various cross-sections of the contours 26 of protuberance 22 may be shaped identically or differently. In another embodiment, the shape of a protuberance is defined by equal arches. In another embodiment, the shape of a protuberance is defined by a variety of arches of different radiuses which are tangent to each other. In another embodiment, the shape of a protuberance is symmetrical. In another embodiment, the shape of a protuberance is asymmetrical. In another embodiment, a protuberance is a bulbous protuberance.

In another embodiment, the invention provides that the device such as footwear 10 supports the foot of a subject only by the two protuberances when the two protuberances are placed on a ground surface. In another embodiment, the invention provides that the device such as footwear 10 supports the foot of a subject during stance only by the two protuberances when the two protuberances are placed on a ground surface. In another embodiment, the invention provides that during stance only the 2 ground engaging surfaces of the protuberances (such as the peak or the surface facing the ground) are in contact with a ground surface. In another embodiment, the invention provides that during stance only the ground engaging surface in each protuberance is in contact with a ground surface.

In another embodiment, at least two bulbous protuberances 22 protrude from a lower surface 24 of support member 12. In another embodiment, only two bulbous protuberances 22 protrude from a lower surface 24 of support member 12. In another embodiment, a lower surface of support member is an outsole. In another embodiment, only two bulbous protuberances 22 protrude from a lower surface 24 of support member 12.

In another embodiment, the ground engaging parts of the device are only the protuberances. In another embodiment, during all phases of gait including the stance phase the protuberances are the only parts of the device which are ground engaging. In another embodiment, during all phases of gait including the stance phase the protuberances 22 are the only parts of the device which are in direct contact with the ground.

In another embodiment, a protuberance as described herein is movable. In another embodiment, a protuberance as described herein is fixed. In another embodiment, a protuberance as described herein is mountable. In another embodiment, a protuberance as described herein is replaceable. In another embodiment, a protuberance as described herein is movable along the outer surface of the support member. In another embodiment, a protuberance as described herein is movable along the outer surface of the outsole. In another embodiment, a protuberance as described herein can be positioned within the outer surface of the support member.

In another embodiment, a protuberance as described herein is movable or translatable such as in a track (e.g., forwards, backwards, sideways or diagonally) and/or rotatable about its own or other axis, or a combination of such motions.

In another embodiment, a protuberance is movable within a predefined area. In another embodiment, a protuberance is movable within an area of 1 $cm^2$ to 18 $cm^2$. In another embodiment, a protuberance is movable within an area of 1 $cm^2$ to 6 $cm^2$. In another embodiment, a protuberance is movable within an area of 1 $cm^2$ to 4 $cm^2$. In another embodiment, a protuberance is movable within an area of 2 $cm^2$ to 8 $cm^2$. In another embodiment, a protuberance is movable within an area of 3 $cm^2$ to 6 $cm^2$. In another embodiment, a protuberance is movable within an area of 4 $cm^2$ to 10 $cm^2$. In another embodiment, a protuberance is movable within an area of 5 $cm^2$ to 18 $cm^2$. In another embodiment, a protuberance is movable within an area of 4 $cm^2$ to 12 $cm^2$.

In another embodiment, a predefined area is a circle. In another embodiment, a predefined area is a square. In another embodiment, a predefined area is an ellipse. In another embodiment, a predefined area is a rectangle. In another embodiment, a predefined area is quadrangular. In another embodiment, a predefined area comprises any shape known to one of skill in the art. In another embodiment, a predefined area is shapeless.

In another embodiment, a protuberance has a base diameter of at least 35 mm. In another embodiment, a protuberance has a base diameter of at least 45 mm. In another embodiment, a protuberance has a base diameter of at least 55 mm. In another embodiment, a protuberance has a base diameter of at least 65 mm. In another embodiment, a protuberance has a base diameter of at least 75 mm. In another embodiment, a protuberance has a base diameter of at least 85 mm. In another embodiment, a protuberance has a base diameter of 35 to 95 mm. In another embodiment, a protuberance has a base diameter of 45 to 105 mm. In another embodiment, a protuberance has a base diameter of 45 to 95 mm. In another embodiment, a protuberance has a base diameter of 55 to 95 mm. In another embodiment, a wider base diameter is used to further stimulate weight bearing. In another embodiment, the flexibility in choosing different base diameters allows balancing a patient suffering from imbalance by stimulating differential weight bearing.

In another embodiment, a protuberance can be positioned anywhere on the support member. In another embodiment, a protuberance can be fixed anywhere on the support member. In another embodiment, a protuberance can be positioned and/or fixed anywhere within a predefined area. In another embodiment, the protuberance is hooked to a rail. In another embodiment, the protuberance is connected to a rail. In another embodiment, the protuberance is connected to a rail and is movable along the rail. In another embodiment, the protuberance is connected to a rail, is movable along the rail, and can be positioned and/or fixed anywhere along the rail.

In another embodiment, a protuberance is slidingly mounted on support member. In another embodiment, a protuberance is mounted on a track 36 (FIG. 2) formed in the lower surface 24 of support member 12, and is selectively positioned anywhere along the track and fastened and or fixed thereto. In another embodiment, track 36 extends along a portion of the shoe sole or all along the length of the shoe sole. Alternatively or additionally, the amount of protrusion of a protuberance is adjusted, such as by mounting protuberance with a threaded fastener 38 (FIG. 3) to support member 12 and tightening or releasing threaded fastener. In another embodiment, the term "fastening", "fixing" and "securing" are used interchangeably.

Figure 3:
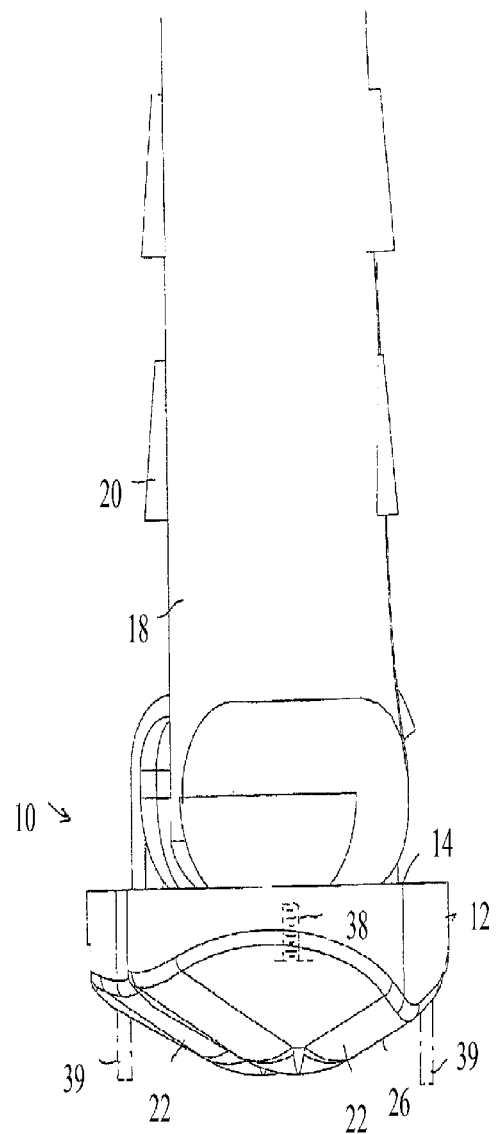

In another embodiment, a device as described herein further comprises an additional bulbous protuberance or bulbous protuberances, non-bulbous protuberance 39, or non-bulbous protuberances shown in FIG. 3. In another embodiment, protuberances 39 are formed in the shape of a peg, stud, bolt, pin, dowel and the like, although the invention is not limited to these shapes. In another embodiment, protuberances 39 may be rigid or flexible. In another embodiment, protuberances 39 are of different resilience or hardness, such as having different elasticity properties or Shore hardness. In another embodiment, protuberances 39 protrude by different amounts from the lower surface 24 of support member 12. In another embodiment, the amount of protrusion of protuberances 39 or height is adjusted. In another embodiment, protuberance 39 is fixable to the sole or movable/relocatable at any place on the lower surface 24 of support member 12.

In another embodiment, a protuberance is slidingly mounted on support member 12. In another embodiment, a device such as footwear 10 comprises a sliding/shifting mechanism for a protuberance inside the sole of footwear 10. In another embodiment, the sliding/shifting mechanism comprises, without limitation, a mechanism that floats in a viscous matrix (e.g., fluid in a chamber formed in the sole), that is suspended by inner cables, or a niche trapping a protuberance with a fixing mean.

Fixing a Protuberance

Figure 2:
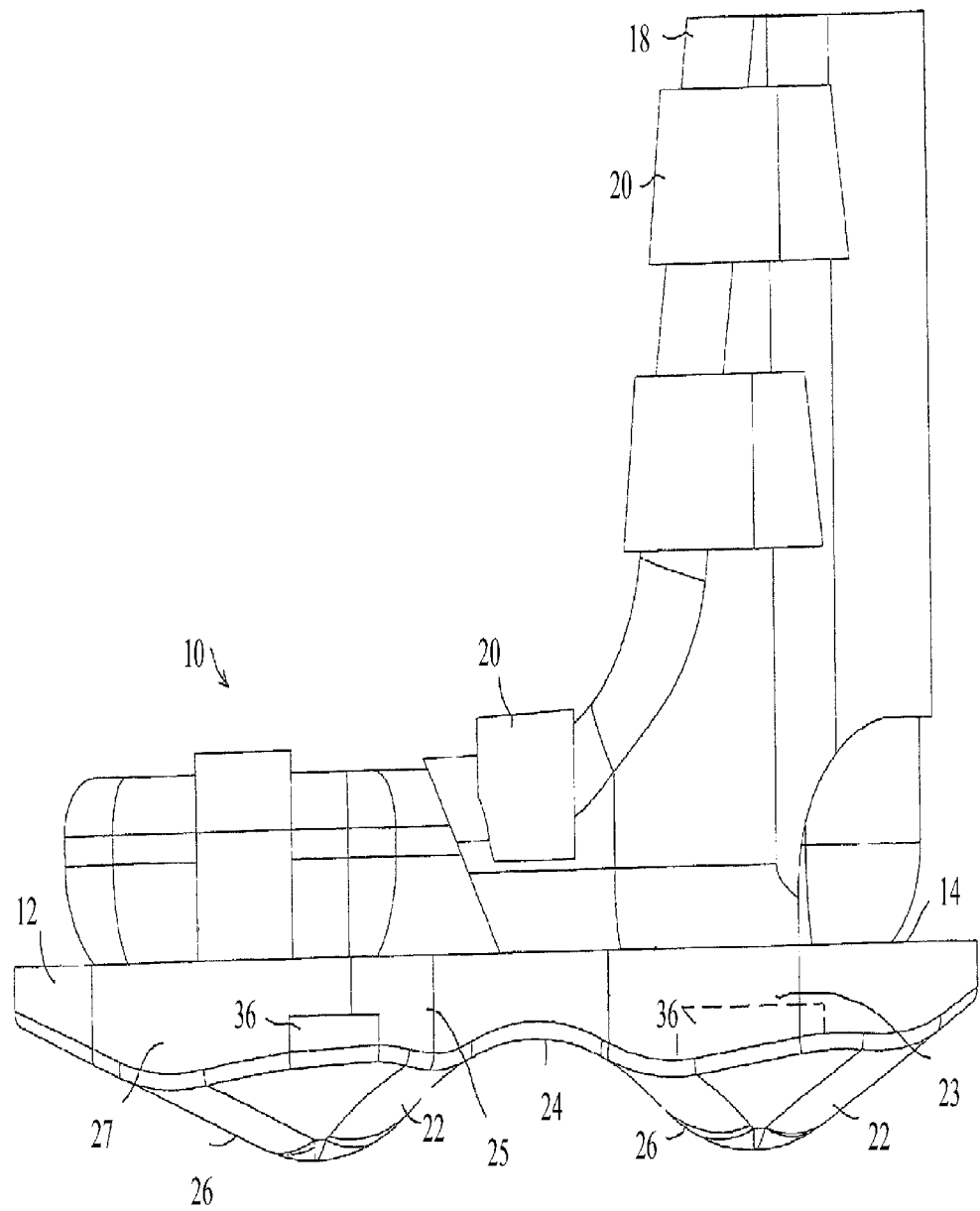
FIGS. 2 and 3 are simplified side-view and rear-view illustrations, respectively, of the footwear of FIG. 1.

As seen clearly in FIG. 2, one protuberance 22 may be positioned more posteriorly than the other protuberance 22. In another embodiment, a device as described herein comprises at least one anterior protuberance. In another embodiment, a device as described herein comprises at least one posterior protuberance. In another embodiment, the device consists of one anterior protuberance and one posterior protuberance. In another embodiment, the device comprises at least one anterior protuberance and one moveable/relocatable posterior protuberance. In another embodiment, the device comprises at least one moveable/relocatable anterior protuberance and one posterior protuberance. In another embodiment, the device comprises at least one moveable/relocatable anterior protuberance and one moveable/relocatable posterior protuberance. In another embodiment, the device consists of one moveable/relocatable anterior protuberance and one moveable/relocatable posterior protuberance.

In another embodiment, the protuberances rise vertically and therefore each protuberance comprises a base end and a peak end. In another embodiment, the surface area of the base is larger than the surface area of the peak. In another embodiment, the peak is the ground engaging portion of a protuberance in the stance phase. In another embodiment, the peak is the ground engaging portion of a protuberance in all gait phases.

In another embodiment, a protuberance such as a bulbous protuberance 22 protrudes from the upper surface 14 of support member 12.

Positions of the Protuberances

Reference is now made, in one embodiment, to FIGS. 1-4, which illustrate footwear 10 constructed and operative in accordance with an embodiment of the present invention. Footwear 10, in one embodiment, is supplied as one or more pairs of shoe-like devices, or alternatively, as just one of the shoe-like devices. In another embodiment, a shoe-like device comprises a shoe platform and protuberances. Footwear 10, in one embodiment, is designed to adapt on a shoe such as Footwear 10. Footwear 10, in one embodiment, is a sandal or sandal-like footwear. In another embodiment, the shoe platform is a boot. In another embodiment, the shoe platform resembles a hiking boot.

In another embodiment, the footwear 10 comprises a support member 12 having a periphery in a shape of a shoe sole with an upper surface 14. In another embodiment, the footwear 10 comprises an insole placed on top of the upper surface 14. In another embodiment, the insole is the interior bottom of footwear 10. In another embodiment, the insole sits directly beneath the foot. In another embodiment, the insole is removable, replaceable, or both. In another embodiment, the insole adds comfort, control the shape, moisture, smell, or any combination thereof. In another embodiment, the insole is placed to correct defects in the natural shape of the foot or positioning of the foot during standing or walking.

In another embodiment, a support member 12 comprises an outsole. In another embodiment, a support member 12 comprises lower surface 24 or an outsole of support member 12. In another embodiment, lower surface 24 or an outsole is made of natural rubber or a synthetic imitation. In another embodiment, lower surface 24 or an outsole comprises a single piece, or may comprise separate pieces of different materials. In another embodiment, lower surface 24 or an outsole can be softer or harder. In another embodiment, a support member 12 further comprises a midsole which is a layer in between the outsole and the insole the most pressure down. In another embodiment, a support member 12 does not have a midsole.

In another embodiment, positioning at least a first bulbous protuberance and a second bulbous protuberance in a balanced position is the position in which the footwear exerts a reduced or the least valgus, varus, (dorsal or plantar) torque about the ankle in a subject being examined. In another embodiment, positioning at least a first bulbous protuberance and a second bulbous protuberance in a balanced position is the position in which the footwear provides the least or minimal lower limbs muscle hyper tonus. In another embodiment, positioning at least a first bulbous protuberance and a second bulbous protuberance in a balanced position is the position in which the footwear provides balanced lower limbs muscle tonus. In another embodiment, positioning at least a first bulbous protuberance and a second bulbous protuberance in a balanced position is the position in which the footwear provides the least or minimal lower limbs muscle hypo tonus. In another embodiment, positioning at least a first bulbous protuberance and a second bulbous protuberance in a balanced position is toning lower limb muscles. In another embodiment, positioning at least a first bulbous protuberance and a second bulbous protuberance in a balanced position is toning the amount of tension or resistance to movement in a muscle involved in gait or other daily functions performed in weight bearing. In another embodiment, positioning at least a first bulbous protuberance and a second bulbous protuberance in a balanced position is lower limb unloading that allows maximal ankle, knee, and hip joint mobility. In another embodiment, positioning at least a first bulbous protuberance and a second bulbous protuberance in a balanced position is providing a reduction of muscle tone, larger passive ankle excursion, improved gait ability, or any combination thereof. In another embodiment, positioning at least a first bulbous protuberance and a second bulbous protuberance in a balanced position is increasing stride length, stance symmetry, or a combination thereof. In another embodiment, positioning at least a first bulbous protuberance and a second bulbous protuberance in a balanced position is increasing the length of the force point of action in lower limb muscles such as but not limited to: soleus, tibialis posterior, and both gastrocnemius muscles. In another embodiment, positioning at least a first bulbous protuberance and a second bulbous protuberance in a balanced position is toning the plantar flexors. In another embodiment, positioning at least a first bulbous protuberance and a second bulbous protuberance in a balanced position is preventing excessive forward rotation as the body moves forward over the stationary foot. In another embodiment, positioning at least a first bulbous protuberance and a second bulbous protuberance in a balanced position is toning the push off of the heel.

Figure 4:
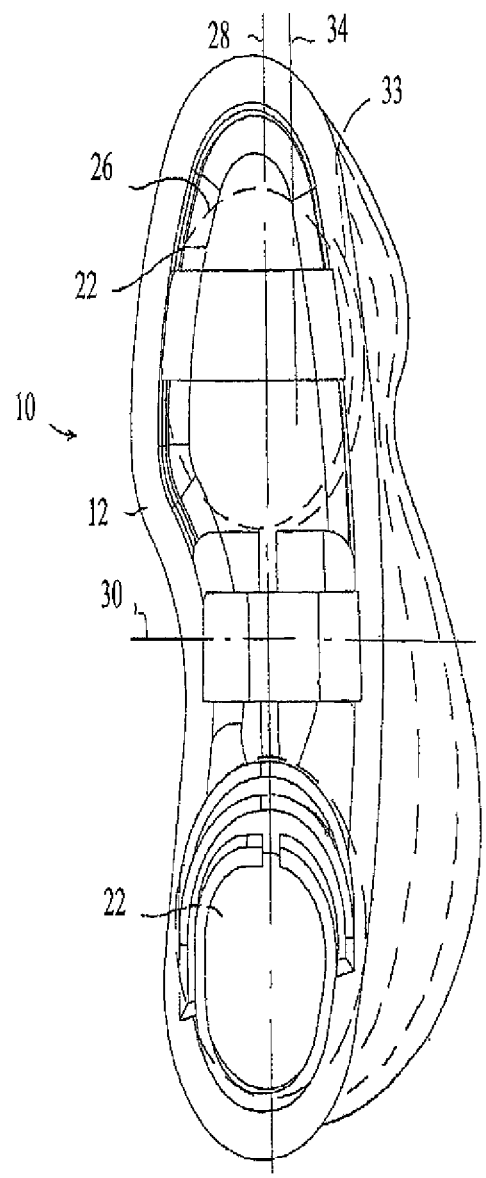
FIG. 4 is a simplified top-view illustration of the footwear of FIG. 1, showing further features of other embodiments of the present invention.

In another embodiment, as seen in FIG. 4, the protuberances are positioned on a common longitudinal axis of support member 12, such as the centerline 28 of support member 12. In another embodiment, the protuberances are positioned on opposite sides of the latitudinal midline 30. In another embodiment, the protuberances are positioned offset from the centerline 28 of support member 12, and on opposite sides of the latitudinal midline 30. In another embodiment, the bases of the protuberances are positioned on the centerline of the support member. In another embodiment, the peaks of the protuberances are positioned on opposite sides of the centerline of support member. In some embodiments, the meaning of "protuberance is positioned offset from the centerline" comprises that the peak or the ground engaging surface of a protuberances is positioned offset from the centerline. In some embodiments, the meaning of "protuberance is positioned offset from the centerline" comprises that only the peak or the ground engaging surface of a protuberances is positioned offset from the centerline but the centerline still crosses the protuberance.

In another embodiment, the peak or the ground engaging surface of the anterior protuberance is positioned laterally from the centerline of the support member. In another embodiment, the peak or the ground engaging surface engages the ground in an upright position. In another embodiment, the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is aligned with centerline. In another embodiment, the peak or the ground engaging surface of the anterior protuberance is positioned medially from the centerline of the support member and the peak or the ground engaging surface of the posterior protuberance is aligned with centerline.

In another embodiment, the peak or the ground engaging surface of the posterior protuberance is positioned laterally from the centerline of the support member. In another embodiment, the peak or the ground engaging surface of the posterior protuberance is positioned medially from the centerline of the support member. In another embodiment, the peak or the ground engaging surface of the posterior protuberance is positioned laterally from the centerline of the support member and the peak or the ground engaging surface of the anterior protuberance is aligned with centerline. In another embodiment, the peak or the ground engaging surface of the posterior protuberance is positioned medially from the centerline of the support member and the peak or the ground engaging surface of the anterior protuberance is aligned with centerline.

In another embodiment, the peak or the ground engaging surface of the posterior protuberance is positioned laterally from the centerline of the support member and the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is positioned medially from the centerline of the support member.

Figure 5:
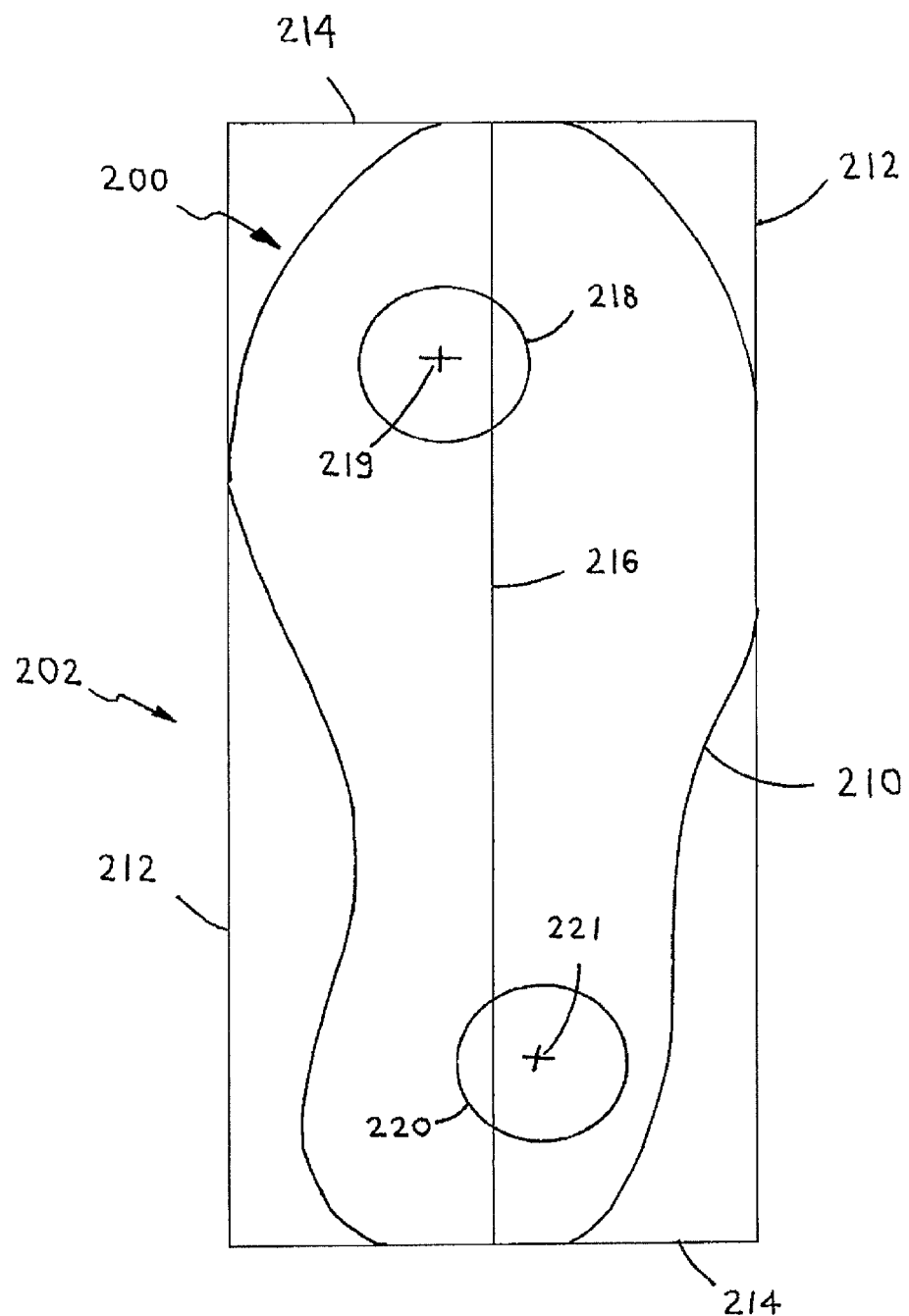
FIG. 5 is a simplified pictorial illustration of an alignment of the anterior (forward) and posterior (rearward) protuberances on a support member, according to embodiments of the present invention.
Figure 6:
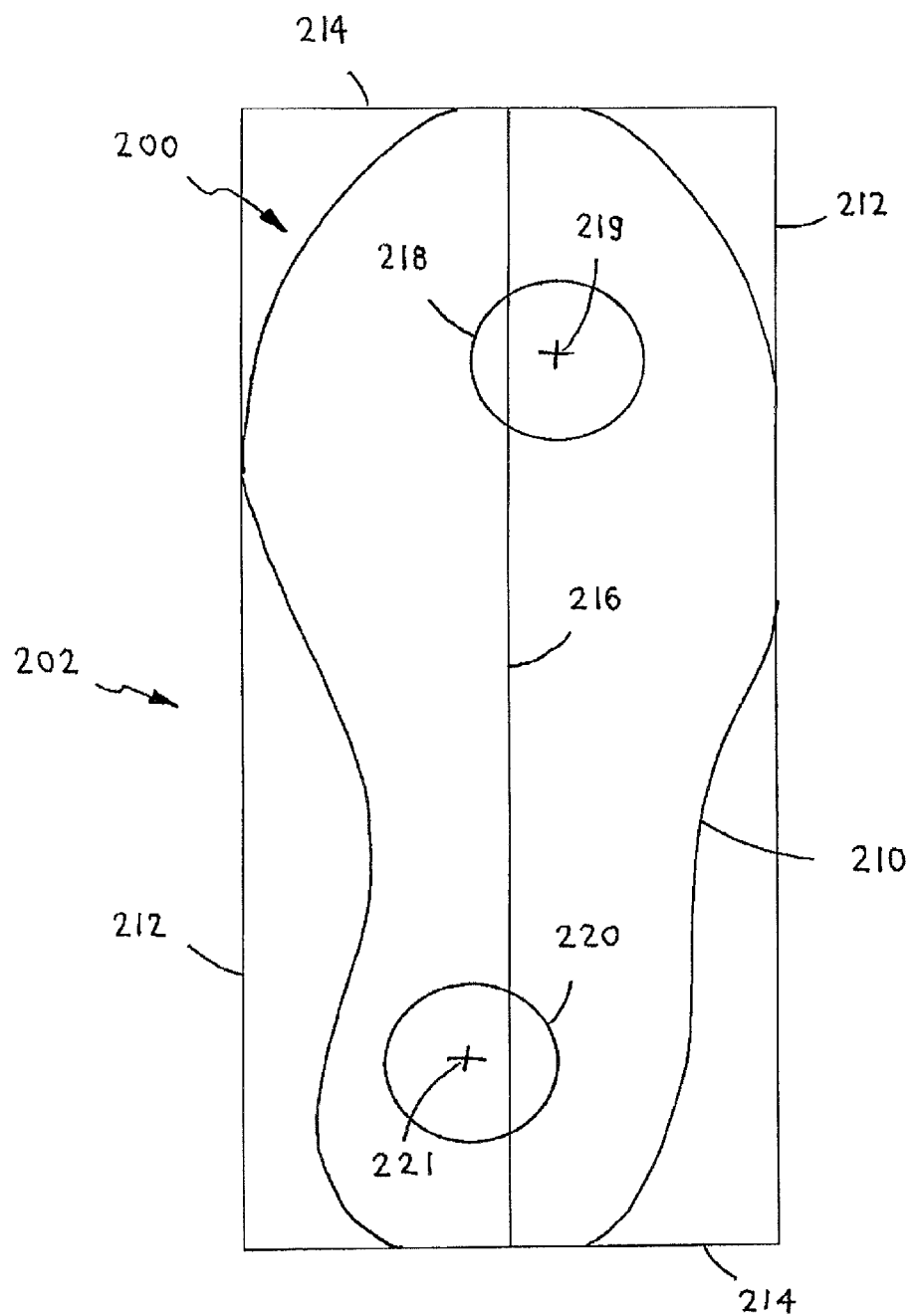
FIG. 6 is a simplified pictorial illustration of another alignment of the anterior and posterior protuberances on a support member, according to embodiments of the present invention.

In another embodiment, the centerline divides longitudinally the calcaneus support portion into two equal halves and further extends towards the phalanges and metatarsals support portion in a straight line. In another embodiment, the centerline divides longitudinally the arch of the calcaneus support portion into two equal halves and further extends towards the phalanges and metatarsals support portion in a straight line. In another embodiment, the centerline divides longitudinally the proximal arch of the calcaneus support portion into two equal halves and further extends towards the phalanges and metatarsals support portion in a straight line. In another embodiment, the centerline divides longitudinally the support portion as seen in FIGS. 5-6 of the calcaneus support portion into two equal halves and further extends towards the phalanges and metatarsals support portion in a straight line. In another embodiment of the present invention, the longitudinal centerline is defined as a longitudinal straight line connecting middles of the short sides of a rectangle which delimits a contour of the support member.

In another embodiment, the bases of the protuberances are positioned on the centerline of the support member and the peaks of the protuberances are positioned on opposite sides of the centerline of support member. In another embodiment, the bases of the protuberances are positioned on the centerline of the support member but the peaks of the protuberances are offset from the centerline of the support member. In another embodiment, the bases of the protuberances are positioned on the centerline of the support member but the peaks of the protuberances are positioned on opposite sides of the centerline of the support member. In another embodiment, positioning a protuberance is positioning the peak or the ground engaging surface of a protuberance. In another embodiment, the terms "peak" and "ground engaging surface" are used interchangeably.

In another embodiment, the anterior protuberance is positioned medially from the centerline of the support member. In another embodiment, the peak of the anterior protuberance is positioned medially from the centerline of the support member. In another embodiment, the base of the anterior protuberance is positioned on the centerline of the support member but the peak of the anterior protuberance is positioned medially from the centerline of the support member. In another embodiment, the anterior protuberance is positioned laterally from the centerline of the support member. In another embodiment, the peak of the anterior protuberance is positioned laterally from the centerline of the support member. In another embodiment, the base of the anterior protuberance is positioned on the centerline of the support member but the peak of the anterior protuberance is positioned laterally from the centerline of the support member. In another embodiment, the posterior protuberance is positioned medially from the centerline of the support member. In another embodiment, the peak of the posterior protuberance is positioned medially from the centerline of the support member. In another embodiment, the base of the posterior protuberance is positioned on the centerline of the support member but the peak of the posterior protuberance is positioned medially from the centerline of the support member. In another embodiment, the posterior protuberance is positioned laterally from the centerline of the support member. In another embodiment, the peak of the posterior protuberance is positioned laterally from the centerline of the support member. In another embodiment, the base of the posterior protuberance is position on the centerline of the support member but the peak of the posterior protuberance is positioned laterally from the centerline of the support member.

In another embodiment, as seen in FIG. 2, the posterior protuberance 22P is positioned generally underneath a calcaneus (heel, ankle) support portion 23 of support member 12. In another embodiment, the anterior protuberance (22A) may be positioned generally underneath a metatarsals support portion 25 and/or phalanges support portion 27 of support member 12.

In another embodiment, as indicated by broken lines 33 in FIG. 4, the anterior protuberances 22A is aligned on a longitudinal axis with its peak offset from centerline 28, and the posterior protuberance (22P) is also is aligned on a longitudinal axis with its peak offset from centerline 28 but to the opposite direction of 22A with respect to centerline 28.

In another embodiment, FIG. 5 is a simplified pictorial illustration of an alignment of the anterior (forward) and posterior (rearward) protuberances on a support member 200, according to embodiments of the present invention. Centerline 216, in the embodiment is defined as a longitudinal straight line (median) that connects the middles of short sides 214 of a rectangle 212, the long sides 212 of which are parallel to centerline 216, and which delimits the contour 210 of the support member. In embodiments of the present invention contour 210 is the contour (254, see FIG. 7) of the foothold confined by the upper part (253, see FIG. 7) of the footwear (250, see FIG. 7), corresponding to the last which is used to form the footwear. In other embodiments of the present invention contour 210 is the outermost contour of the footwear. In other embodiments of the present invention contour 210 is the contour of the bottom surface of the sole of the footwear. In some embodiments, the terms "forward" and "anterior" are used interchangeably. In some embodiments, the terms "rearward" and "posterior" are used interchangeably.

According to embodiments of the present invention, as shown in FIG. 5, forward protuberance 218 at the anterior (phalanges) portion of the support member (i.e. its front portion) is positioned medially offset to centerline 216. By "medially offset" is meant that a peak surface (which can be the ground engaging surface) of protuberance 218 (marked by cross 219) is shifted from centerline 216 medially towards the inner side of support surface 200, facing the support member of the other foot (not shown in this figure). The peak surface is a surface on the protuberance which is furthest from the support surface with respect to other surfaces of the protuberance.

According to embodiments of the present invention, as shown in FIG. 5, rearward (posterior) protuberance 220 at the posterior (calcaneus) portion of the support member (i.e. its back portion) is positioned laterally offset to centerline 216. By "laterally offset" is meant that a peak surface (which can be the ground engaging surface) of protuberance 220 (marked by cross 221) is shifted from centerline 216 laterally towards the outer side of support surface 200, away from the support member of the other foot (not shown in this figure).

The alignment of the protuberances shown in FIGS. 5 and 6 is useful, for example, for tuning pelvic muscles.

FIG. 6 is a simplified pictorial illustration of another alignment of the anterior and posterior protuberances on a support member, according to embodiments of the present invention. According to embodiments of the present invention, as shown in FIG. 6, forward (anterior) protuberance 218 is laterally offset to centerline 216, whereas rearward protuberance 220 is medially offset to centerline 216.

Figure 7:
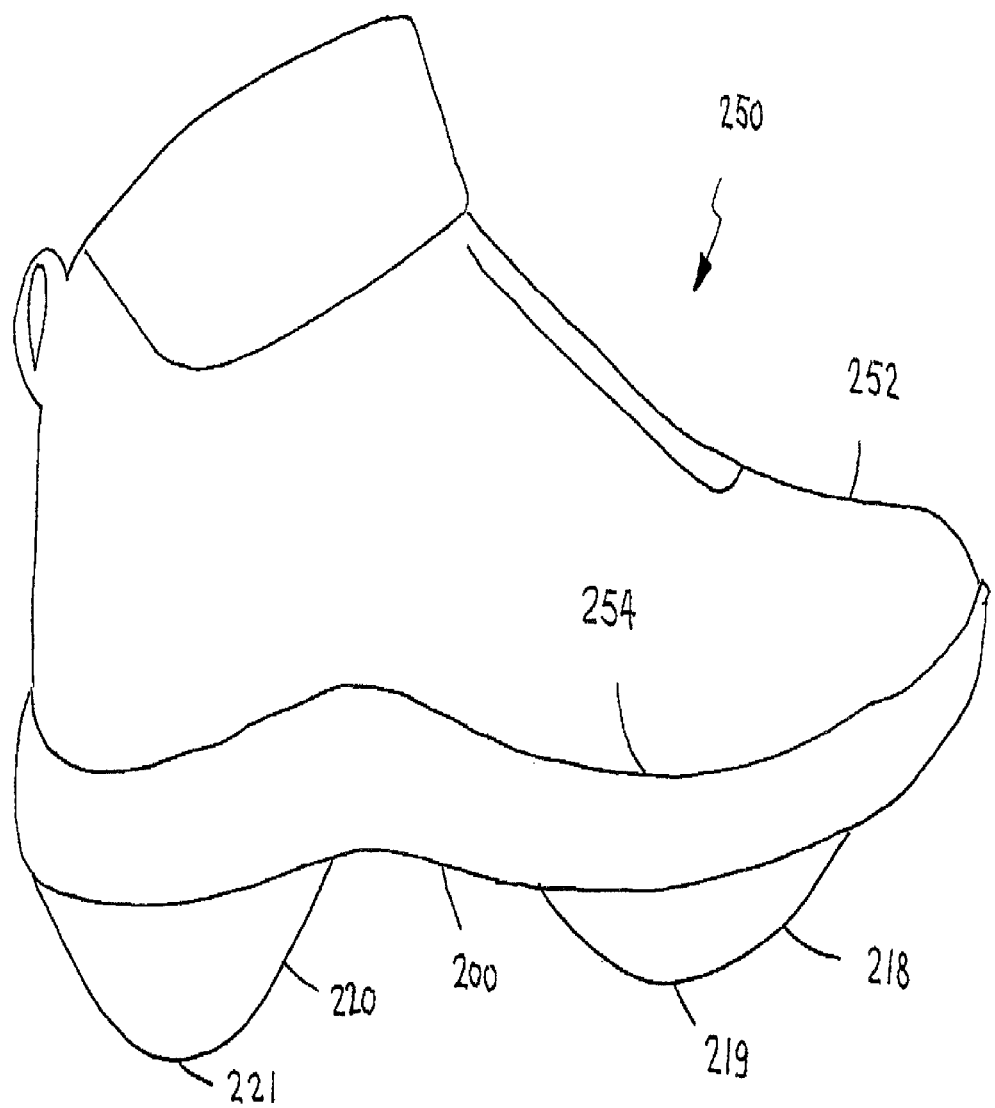
FIG. 7 is a simplified pictorial illustration of a sneaker constructed and operative in accordance with an embodiment of the present invention, whose rearward protuberance has a greater height than the height of the forward protuberance.

FIG. 7 is a simplified pictorial illustration of a sneaker 250 constructed and operative in accordance with an embodiment of the present invention, whose rearward protuberance 220 has a greater height (protrusion) than the height of the forward protuberance 218. It is noticeable that such arrangement facilitates initial contact between rearward protuberance 220 and the supporting ground (not shown in this figure) when a user wears the sneaker, before the forward protuberance is brought in contact with the ground. When both protuberances are placed in contact with the ground the foot of the user wearing sneaker 250 acquires a downward inclination with respect to direction of gait of the user.

Figure 8:
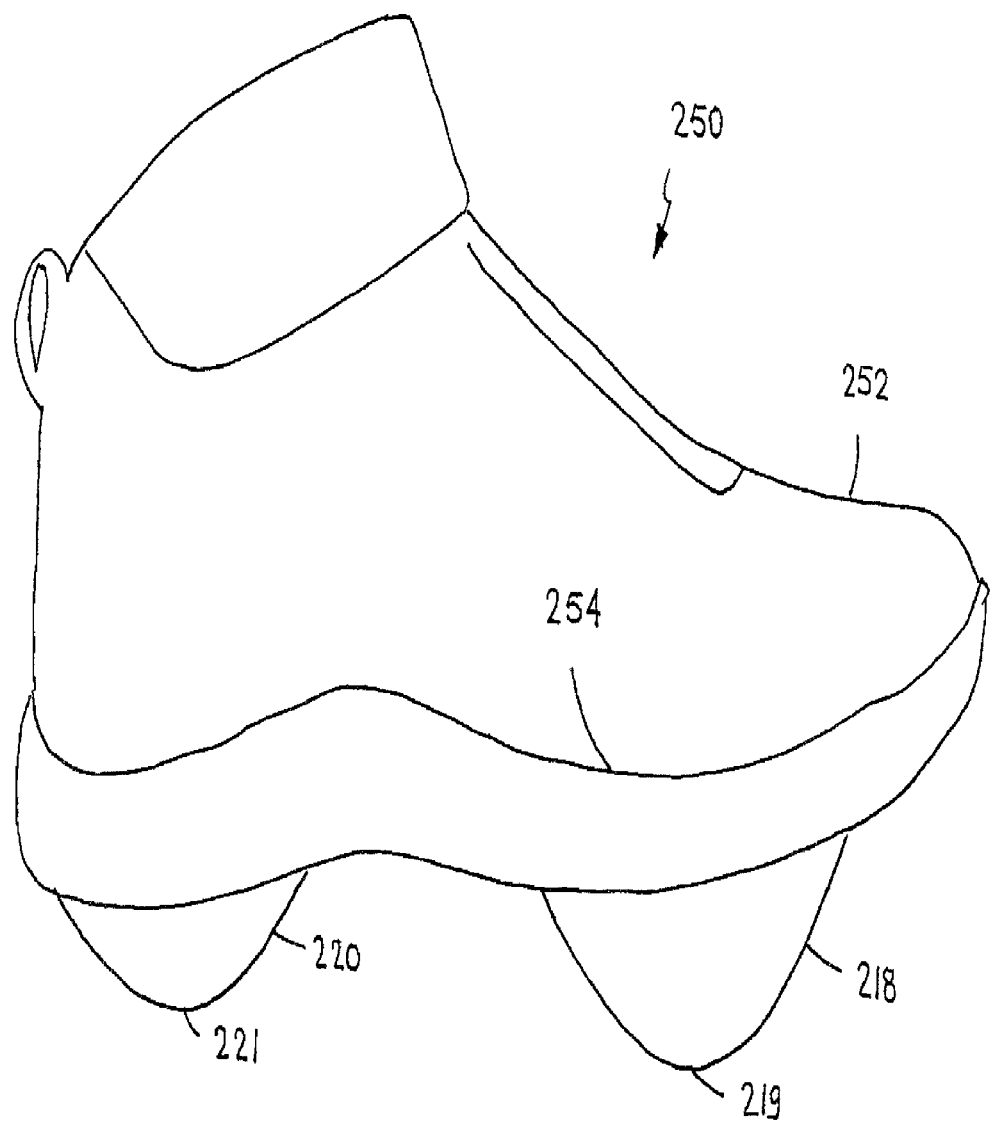
FIG. 8 is a simplified pictorial illustration of a sneaker constructed and operative in accordance with an embodiment of the present invention, whose forward protuberance has a greater height than the height of the rearward protuberance.

FIG. 8 is a simplified pictorial illustration of a sneaker 250 constructed and operative in accordance with an embodiment of the present invention, whose forward protuberance 218 has a greater height than the height of the rearward protuberance 220. In this embodiment when only the posterior protuberance is in contact with the ground (the heel rocker during the initial contact phase of the gait cycle) there is a smaller distance between the anterior protuberance and the ground. In this embodiment the rocking movement of the foot is reduced when the user wears the sneaker. In this embodiment when both protuberances are placed in contact with the ground the foot of the user wearing sneaker 250 acquires an upward inclination (with respect to the direction of gait of the user).

Figure 9:
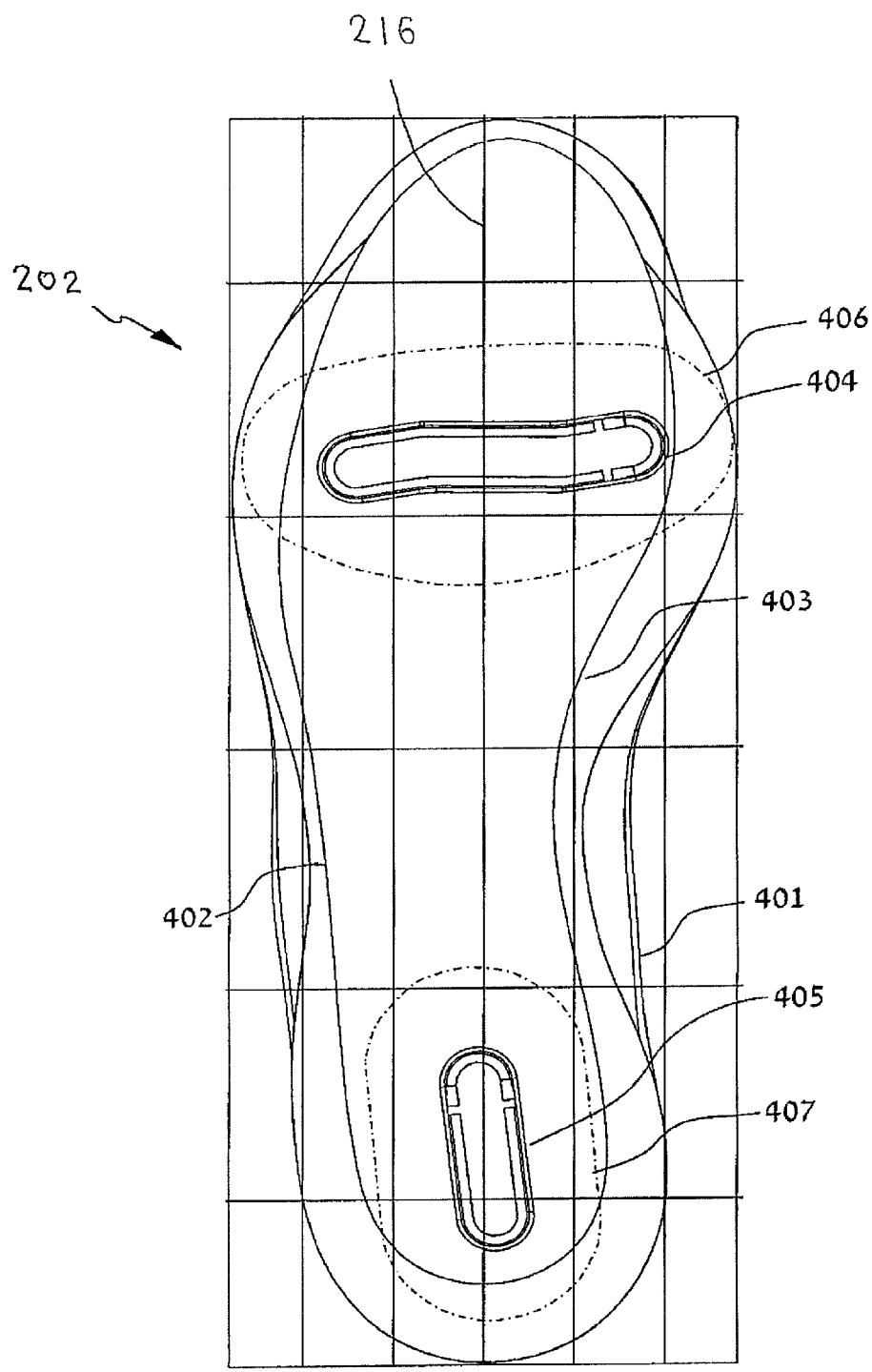
FIG. 9 illustrates maximal area boundaries of positioning of the center of the anterior and posterior protuberances with respect to a support surface, according to embodiments of the present invention.

FIG. 9 illustrates maximal area boundaries of positioning of the anterior and posterior protuberances with respect to a support surface, according to embodiments of the present invention. Shown in this figure is a bottom view of a sneaker designed to be worn on a right foot of a user. The medial side is thus the right side of the drawing, facing the arc of greater curvature of the side arcs of the sneaker. The lateral side is opposite to the medial side that is the left side of the drawing, facing the arc of lesser curvature of the side arcs of the sneaker. Indicated are the midsole 401 and last/shoe 402, contour 403 of the foothold which is determined by the last used in the making of the sneaker. Front rail 404 and rear rail 405 are used for anchoring the protuberance. The area bordered by dotted line 406 marks the maximal area within which the peak surface of the anterior protuberance, i.e. the ground engaging surface of the anterior protuberance, may be located, according to some embodiments of the present invention. The area bordered by dotted line 407 marks the maximal area within which the peak surface of the posterior protuberance.

Figure 10:
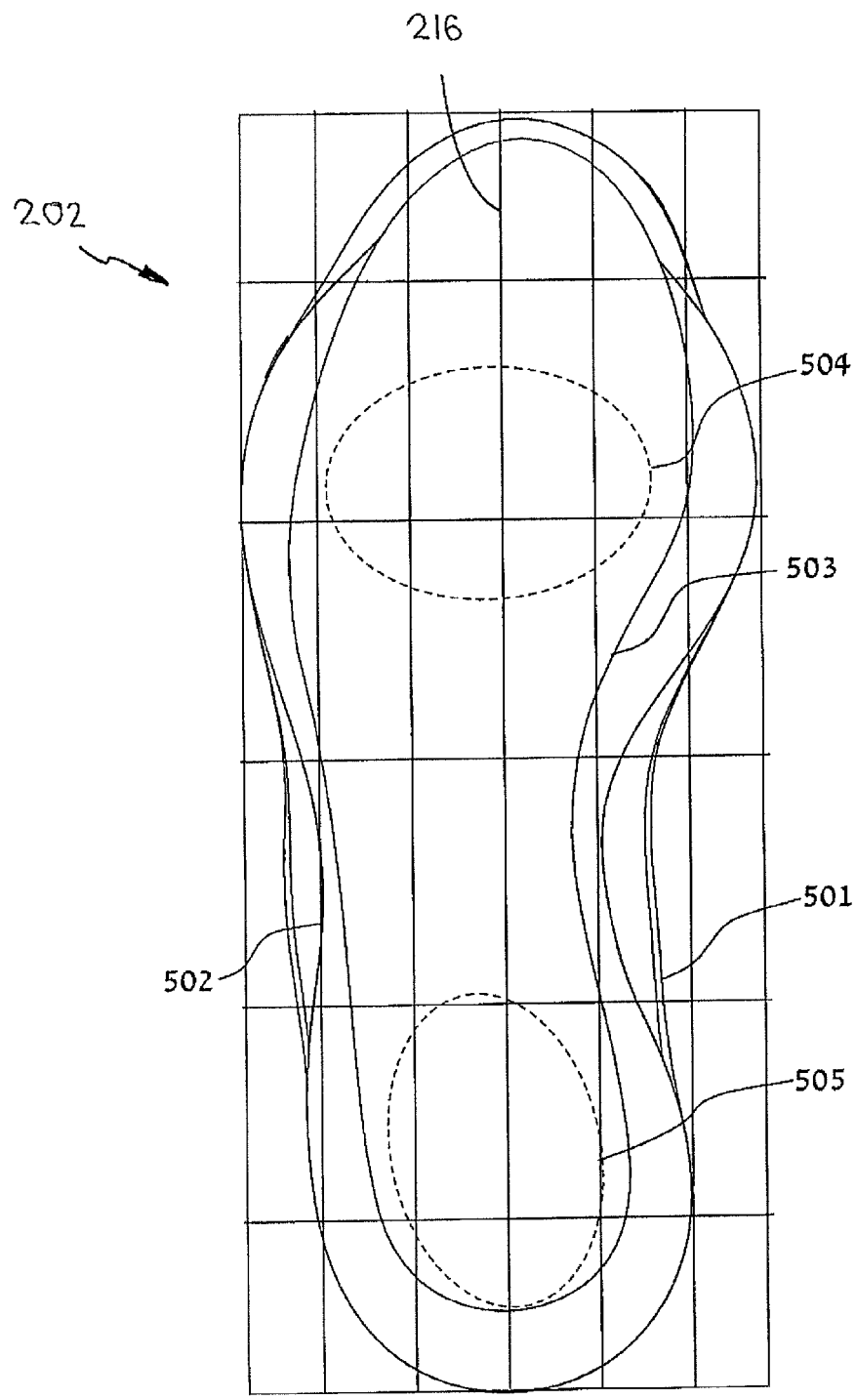
FIG. 10 illustrates effective area boundaries of positioning of the center of the anterior and posterior protuberances with respect to a support surface, according to embodiments of the present invention.

FIG. 10 illustrates the effective area boundaries of positioning of the anterior and posterior protuberances with respect to a support surface, according to embodiments of the present invention. Indicated are the midsole 501 and outsole 502, contour 503 of the foothold which is determined by the last used in the making of the sneaker. The area bordered by dotted line 504 marks the effective area within which the peak surface of the anterior protuberance, i.e. the ground engaging surface of the anterior protuberance, may be located, according to some embodiments of the present invention. The area bordered by dotted line 505 marks the effective area within which the peak surface of the posterior protuberance. "Effective" refers to the effectiveness of use of the footwear according to embodiments of the present invention, which facilitates treatment. For clarity both FIGS. 9 and 10 are divided to 36 equal parts. The effective locations will be within the same parts regardless of sizing.

Figure 11:
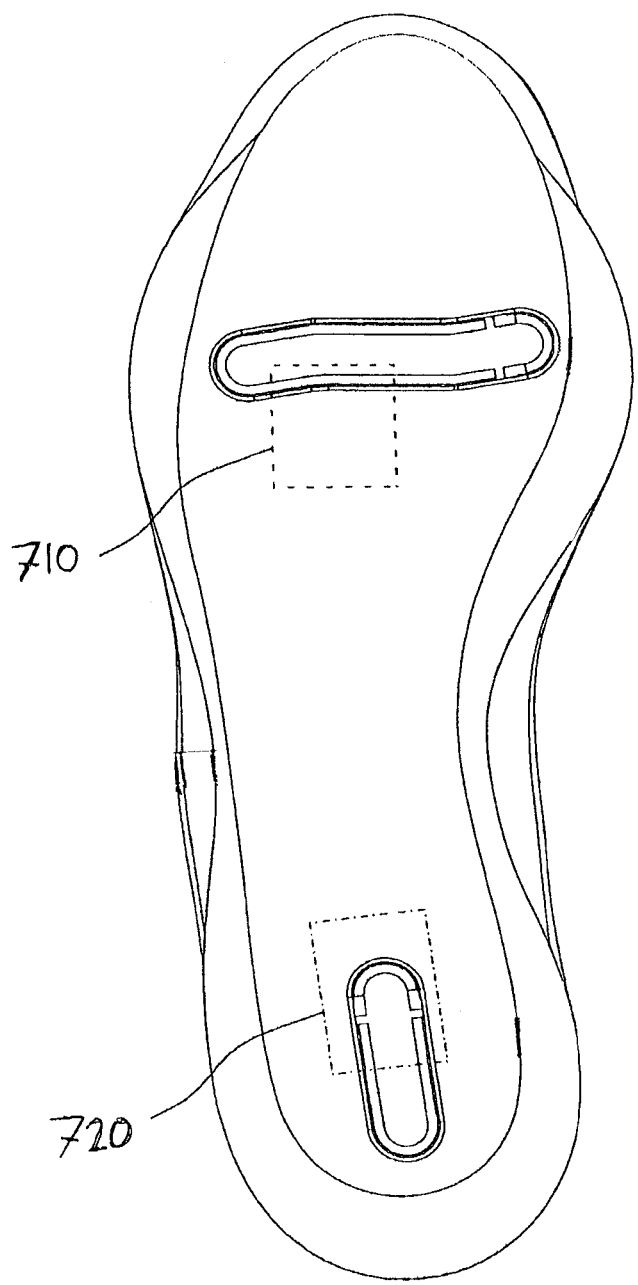
FIG. 11 illustrates effective area boundaries of positioning of the center of the anterior and posterior protuberances with respect to a support surface, according to embodiments of the present invention.

FIG. 11 illustrates the effective area boundaries of positioning of the anterior and posterior protuberances with respect to a support surface, according to embodiments of the present invention which include treatment and/or improvement of function and/or alleviation of pain for a subject afflicted with a neurological conditions. Indicated is the area bordered by dotted line 710 which marks the effective area within which the peak surface of the anterior protuberance, i.e. the ground engaging surface of the anterior protuberance, may be located, while treating or alleviating pain for the diseases and/or conditions described for FIG. 11 hereinabove. Indicated is the area bordered by dotted line 720 which marks the effective area within which the peak surface of the posterior protuberance, i.e. the ground engaging surface of the posterior protuberance, may be located, while treating or improving function or alleviating pain for the diseases and/or conditions described for FIG. 11 hereinabove. The areas bordered by dotted lines 710 and 720 are within the areas bordered by dotted lines 504 and 505, respectively, in FIG. 10. As provided before, FIG. 10 is divided to 36 equal parts. The effective locations will be within these effective parts regardless of sizing. Each possibility represents a separate embodiment of the present invention.

Figure 12:
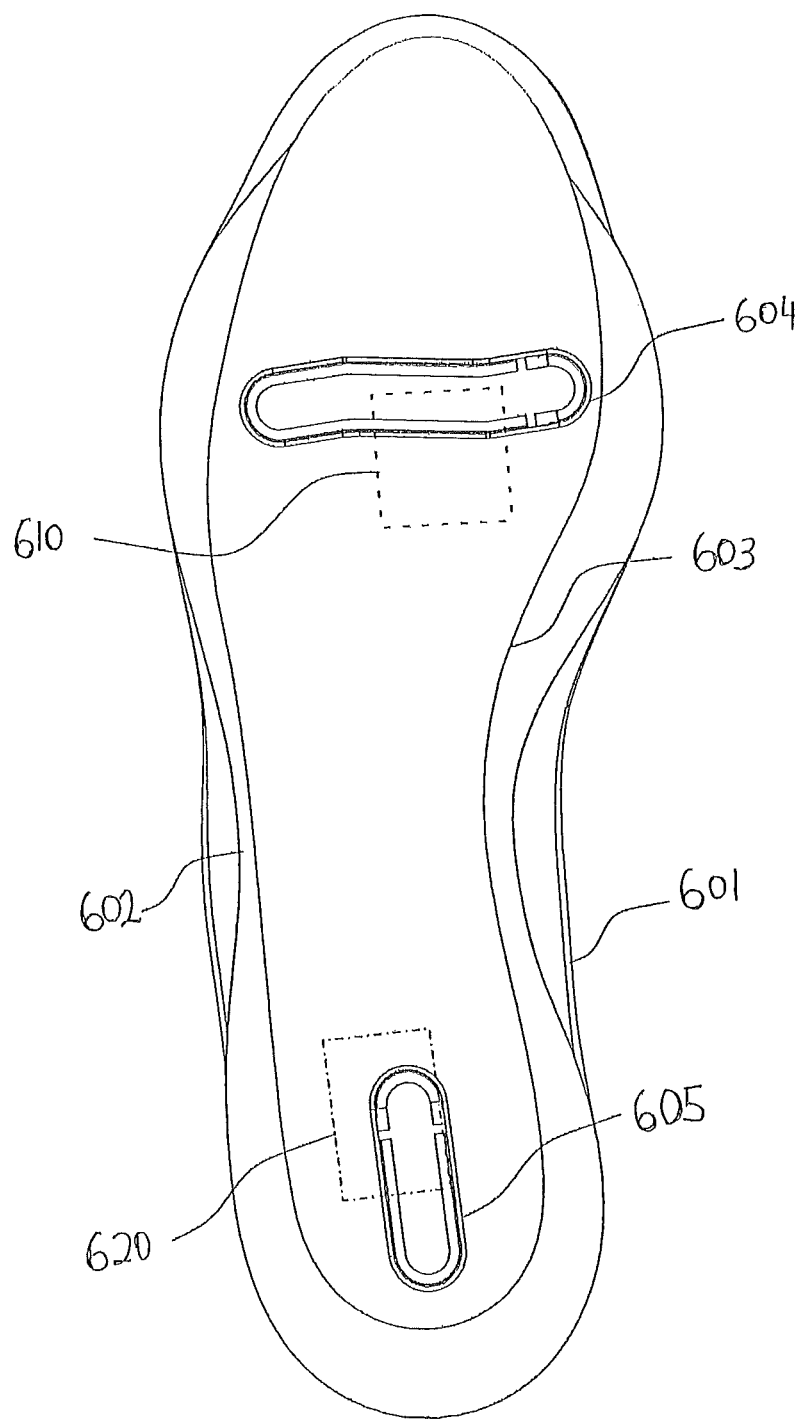
FIG. 12 illustrates effective area boundaries of positioning of the center of the anterior and posterior protuberances with respect to a support surface, according to some embodiments of the present invention.

FIG. 12 illustrates the effective area boundaries of positioning of the anterior and posterior protuberances with respect to a support surface, according to embodiments of the present invention which include treatment and/or improvement of function and/or alleviation of pain of a subject having a neurological condition. Indicated are the midsole 601 and outsole 602, last 603 of the foothold which is determined by the last used in the making of the sneaker. Front rail 604 and rear rail 605 are used for anchoring the protuberance. Indicated is the area bordered by dotted line 610 which marks the effective area within which the peak surface of the anterior protuberance, i.e. the ground engaging surface of the anterior protuberance, may be located, while treating or alleviating pain for the diseases and/or conditions described for FIG. 12 hereinabove. Indicated is the area bordered by dotted line 620 which marks the effective area within which the peak surface of the posterior protuberance, i.e. the ground engaging surface of the posterior protuberance, may be located, while treating or improving function or alleviating pain for the diseases and/or conditions described for FIG. 12 hereinabove. The areas bordered by dotted lines 610 and 620 are within the areas bordered by dotted lines 504 and 505, respectively, in FIG. 10. As provided before, FIG. 10 is divided to 36 equal parts. The effective locations will be within these effective parts regardless of sizing. Each possibility represents a separate embodiment of the present invention.

Figure 13A:
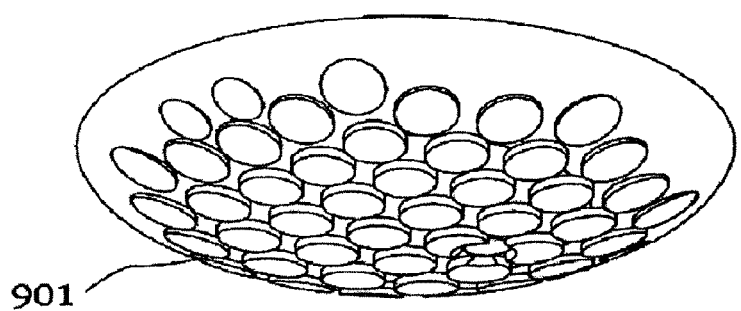
FIG. 13A is an isometric view of a protuberance suitable for use on a footwear, according to embodiments of the present invention.
Figure 13B:
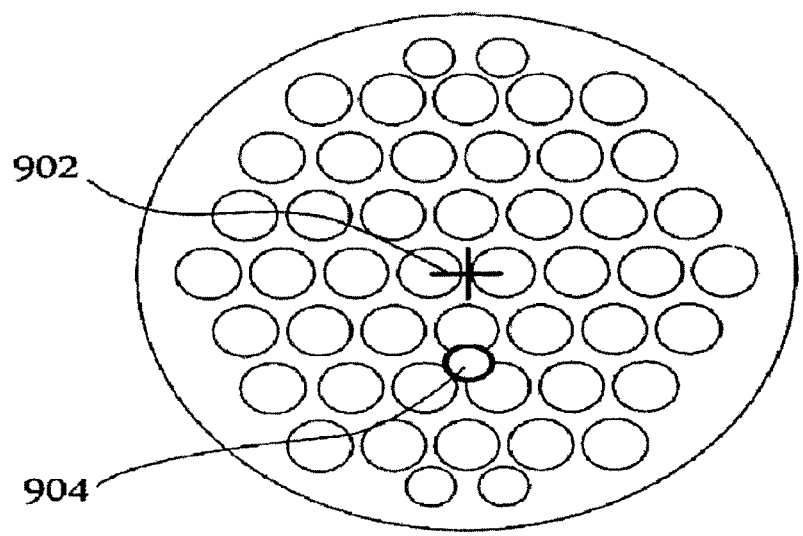
FIG. 13B is a frontal view of a protuberance suitable for use on a footwear, according to embodiments of the present invention.
Figure 13C:
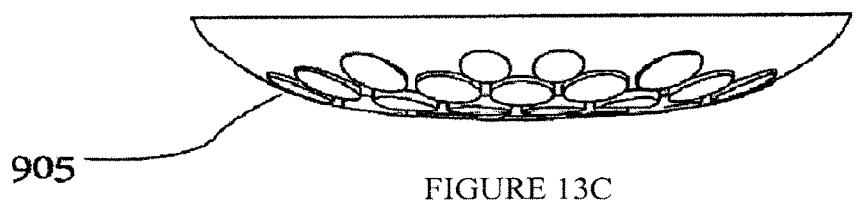
FIG. 13C is a side view of a protuberance suitable for use on a footwear, according to embodiments of the present invention.

FIG. 13A is an isometric view of a protuberance suitable for use on a footwear, according to embodiments of the present invention. Cleats 901, according to embodiments of the present invention, cover the ground engaging area of a protuberance, for facilitating enhanced grip of the surface on which the user stands or walks. FIG. 13B is a frontal view of a protuberance suitable for use on a footwear, according to embodiments of the present invention. The peak surface is marked by cross 902. Bore 904 is provided for a screw or other fastening arrangement to fix the protuberance in the desired position. FIG. 13C is a side view of a protuberance suitable for use on a footwear, according to embodiments of the present invention. Convexity 905 of the protuberance is clearly seen. Various convexities may be employed, all of which define a peak surface, typically (but not necessarily) at the center of the protuberance, which is the surface which comes in contact with the ground, when the user attaches the support member to the foot, and walks or stands on the ground.

FIG. 13 is a simplified pictorial illustration of a protuberance according to embodiments of the present invention. As shown a protuberance is convex 905 (13C). Each protuberance, according to embodiments of the present invention, comprises a fixing hole (for fixing a protuberance) 904 in which a latch, a bolt, or a screw is placed therein. The peak of a protuberance, which in some embodiments of the present invention, is placed within the center of the ground engaging area 902 is in contact with the ground during stance (13B).

Resilience, Hardness, and Elasticity

In another embodiment, calibrating comprises positioning a protuberance on a support member. In another embodiment, calibrating comprises adjusting the height or protrusion of a protuberance. In another embodiment, calibrating comprises adjusting a resilience of a protuberance. In another embodiment, calibrating comprises adjusting a hardness of a protuberance. In another embodiment, calibrating comprises adjusting an elasticity of a protuberance.

In another embodiment, a protuberance is compressible. In another embodiment, a protuberance is deformable. In another embodiment, a protuberance is compressible or deformable upon pressure exerted by subject's weight.

In another embodiment, a protuberance is constructed of any suitable material, such as but not limited to, elastomers or metal or a combination of materials, and have different properties. In another embodiment, a protuberance comprises different resilience or hardness, such as having different elasticity properties or Shore hardness.

In another embodiment, a protuberance comprises spikes or grip means for providing better stability. In another embodiment, a protuberance comprises spikes or grip means as anti-slippery means. In another embodiment, FIG. 13 provides a protuberance comprising small rounded grip means. In another embodiment, spikes or grip means are constructed of any suitable material, such as but not limited to: elastomers such as rubbers or plastic materials. In another embodiment, spikes or grip means cover only a portion of a protuberance. In another embodiment, spikes or grip means cover at least a ground engaging surface of a protuberance (the surface in contact with the ground during stance). In another embodiment, a fixing means for securing a protuberance to the support portion is embedded within a spikes or a grip means. In another embodiment, a fixing means for securing a protuberance to the support portion is places in between spikes or a grip means.

In another embodiment, a protuberance has a shore hardness of between 30 to 90 Sh A. In another embodiment, a protuberance has a shore hardness of between 40 to 55 Sh A. In another embodiment, a protuberance has a shore hardness of between 50 to 70 Sh A. In another embodiment, a protuberance has a shore hardness of between 65 to 90 Sh A. In another embodiment, a protuberance has a shore hardness of between 55 to 60 Sh A. In another embodiment, a protuberance has a shore hardness of between 65 to 70 Sh A. In another embodiment, an anterior and a posterior protuberance comprise identical shore hardness. In another embodiment, an anterior and a posterior protuberance comprise different shore hardness.

In another embodiment, a protuberance is a soft protuberance comprising a shore hardness of between 40 to 55 Sh A. In another embodiment, a protuberance is a medium hardness protuberance comprising a shore hardness of between 50 to 70 Sh A. In another embodiment, a protuberance is a hard protuberance comprising a shore hardness of between 65 to 90 Sh A.

In another embodiment, a protuberance has an abrasion between 1-60 mm$^3$ (by DIN 53516). In another embodiment, a protuberance comprises a rubber cup. In another embodiment, a protuberance comprises natural rubber compounds. In another embodiment, a protuberance comprises synthetic rubber compounds such as TPU, PU or TPR. In another embodiment, a protuberance comprises silicone. In another embodiment, a protuberance a plastic material such as PA 6 (nylon), PA6/6 (nylon)+glass fiber, ABS, Polypropylene, POM (Polyoxymethylene). In another embodiment, a protuberance comprises a metal such as aluminum, steel, stainless steel, brass, or metal alloys. In another embodiment, a protuberance comprises compound materials such as glass fibers, carbon fibers, aramid fibers (e.g., Kevlar®), or any combination thereof.

Adjustments

In another embodiment, different heights of a protuberance can be used. In another embodiment, a height of a protuberance is correlative or equal to the amount of protrusion. In another embodiment, the amount of protrusion is the distance from the surface of the support member to the ground engaging portion of a protuberance. In another embodiment, the amount of protrusion is the distance from the surface of the support member to the most distant ground engaging portion of a protuberance. In another embodiment, height is calibrated by adding a spacer between a protuberance and the outsole. In another embodiment, different weights of a protuberance can be used. In another embodiment, weight is calibrated by adding a spacer between a protuberance and the outsole.

In another embodiment, height is calibrated by adding a spacer between a protuberance and the outsole. In another embodiment, different weights of a protuberance can be used. In another embodiment, weight is calibrated by adding a weighted disc/spacer between a protuberance and the outsole. In another embodiment, in order to assist the clearance during right leg swing additional height is added to the left BPs and vice versa.

In another embodiment, the height of the anterior protuberance differs from the height of the posterior protuberance. In another embodiment, the height of the anterior protuberance or of the posterior protuberance is adjusted with spacers positioned between the support member or the outsole and the base portion of a protuberance. In another embodiment, a spacer is fixed (for enhancing protrusion by increasing height) between the outsole and base portion of a protuberance.

In another embodiment, a spacer or a protuberance comprises a diameter of 50-150 mm. In another embodiment, a spacer or a protuberance comprises a diameter of 55-110 mm. In another embodiment, a spacer or a protuberance comprises a diameter of 60-100 mm. In another embodiment, a spacer or a protuberance comprises a diameter of 80-90 mm. In another embodiment, a spacer or a protuberance comprises a diameter of 85 mm. In another embodiment, a spacer or a protuberance comprises a thickness of 1-12 mm. In another embodiment, a spacer or a protuberance comprises a thickness of 1-4 mm. In another embodiment, a spacer or a protuberance comprises a thickness of 3-10 mm. In another embodiment, a spacer or a protuberance comprises a thickness of 1-3 mm. In another embodiment, a spacer or a protuberance comprises hardness of 60-70 Shore A, which is a soft spacer. In another embodiment, a spacer or a protuberance comprises hardness of 90-100 Shore A, which is a hard spacer. In another embodiment, a spacer or a protuberance comprises hardness of 71-89 Shore A, which is medium hardness spacer.

In another embodiment, a spacer or a protuberance weighs 2-500 g. In another embodiment, a spacer or a protuberance weighs 2-250 g. In another embodiment, a spacer or a protuberance weighs 2-6 g. In another embodiment, a spacer or a protuberance weighs 2-20 g. In another embodiment, a spacer or a protuberance weighs 2-20 g is made of Nylon. In another embodiment, a spacer or a protuberance weighs 2-20 g is made of Nylon and fiber. In another embodiment, a spacer or a protuberance weighs 2-40 g is made of Nylon and glass fiber. In another embodiment, a spacer or a protuberance weighs 30-100 g. In another embodiment, a spacer or a protuberance weighs 50-80 g. In another embodiment, a spacer or a protuberance weighs 60-100 g. In another embodiment, a spacer or a protuberance comprises: Nylon glass fiber polyurethane an alloy (such as but not limited to Zink alloy), or any combination thereof.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Pain Evaluation

In all case studies, pain is presented as graded by the patient on a 10 cm Visual analogue scale (VAS). The ends of the scale were defined as 0—no pain and 10—worst pain imaginable. A pain of 4/10 means 4 cm out of 10 cm.

Positioning Method

After each change (calibration, positioning) in the configuration of the protuberances attached to the footwear, the patient was asked to walk a distance of 20 meters in order to verify that the patient remains balanced and that the change in configuration resulted in a desired effect (for example, reduction in pain, improvement of timing of the heel-strike, improved control of knee motion, and the like).

Prescribing the Device

The device comprises 2 units of footwear: one for the left foot and one for the right foot. The footwear used is a light walking boot.

Prescription included a set of instructions to the patients. These instructions included: duration of wearing the device per day (usually 30-60 minutes daily). Daily uses included wearing the device during routine activities at home or work, that may include watching TV, computer activities; eating activities, and the like. Actual weight bearing (walking, standing etc.) constituted 10-25% of 30-60 minutes. Thus, if the patient has worn the device for 60 minutes per day, total of 5-10 minutes were dedicated, accumulatively, to weight bearing activities. This ensures a gradual process of getting accustomed to walking with the system whilst maintaining the functionality of the treatment. In this manner any adverse effects, such as muscle cramps and muscle pain, can be avoided.

Gait Measurements

Gait measurements below includes spatio-temporal measurements performed by various computerized mats as well as three-dimensional gait labs or other gait lab that are able to measure velocity, step length and single limb support. Unless noted otherwise, the gait lab is done when patient is barefoot.

In the studies below, physiological values of Single Limb Support are between 38%-40% of the step cycle. In some pathologies (e.g. reduced sensory input, central or neurological pain, and the like), the single limb support is usually lower than 40% and sometimes lower than 38%. In other pathologies (e.g. hyper-mobility of the joints and/or poor proximal (pelvic) control) single limb support is usually higher than 40%.

In the "pain" section of the calibrations a repeated shift is described in order to bring the patient to a reduced pain calibration. In some cases, a shift of a protuberance(s) of 2 mm is repeated between 1-3 times until reaching the desired effect. In some cases, the process can include shifting more than 3 times of over 2 mm, to eventually 1 cm or more from the "Balanced" position, until the desired effect is achieved. As long as the shift does not result in excessive eversion or inversion.

Example 1

Treatment of a Subject (Patient) Having a Parkinson's Disease with Lt Hip and Bilateral Knee Pain A 47 years old male patient having Parkinson's disease was presented to the treatment center with a main complaint of slowness in gait and chorea.

Case History: Patient complains of suffering from a gradually deteriorating gait as well as feeling unstable and insecure during ambulation. He has been diagnosed with Parkinson's disease 11 years prior to his initial consultation and started treatment with L-dopa. A few months following the commencement of medications choreatic movements appeared which were unresponsive to any changes in dosage. In addition, he reported he developed pain in the left hip (VAS 6/10) which increases during walking and standing. He also had pain in both knees (VAS 5/10) in walking as well as going up or down stairs. This pain, which increased in weight bearing activities, further, limited his function.

Physical Examination: On observation, the patient was in simian stance. Choreatic movements were apparent in the upper torso and around the pelvis. The knees were in a flexed position (−5 degrees). When his balance reactions were tested the patient was unable to stand on one leg and exhibited increased postural sway in Romberg test with a tendency to sway in the posterior direction. Lumbar ranges of motion were full except extension which was limited to 50% of normal range but produced no pain. Hip assessment revealed full ranges of motion bilaterally with a positive FADIR test (VAS 2/10) on the left. Knee assessment did not reproduce his symptoms but showed moderate crepitus in both patellofemoral joints. Clinical gait assessment showed the patient ambulated with a low clearance during the swing phase (shuffle gait, typical of Parkinson's disease). The choreatic movements decreased during walking, but the patient reported he felt the hip and knee pain rated verbally at a level of 4/10.

Imaging and Gait Lab: Knee X-ray in standing: no radiological findings. Hip X-rays: no radiological findings. Gait lab results (Table 1) showed velocity of 104.5 cm/sec, single limb support of 35.5% (measured in % of gait cycle) in the left leg and 38.3% in the right leg. Step length: Left: 58.6 cm Right: 60 cm.

Therapy: Bulbous protuberances (BP's): Identical BP's with a low convexity (B) and hard resilience were attached and fixed to the patients' device under the hind foot of the right and left devices. In order to increase his stability, a weighted disc (100 grams) was attached and fixed between the posterior BP's and the patients' device under the hind foot of the left and right units. In order to maintain a neutral ankle position, a hard 2 mm spacer and a soft 2 mm spacer were attached and fixed between the sole of the right foot and the left foot units and the anterior BP's. The anterior BP's were also calibrated with a B convexity and hard resilience.

Balancing Process: The patient's device was calibrated and fine tuned during repeated clinical gait assessments. During this process, care is taken to reduce the eversion and inversion during heel strike, loading response, mid-stance and toe-off.

Pain: In order to reduce pain in the left hip, the posterior left BP was calibrated 1-2 mm to a more posterior position and fixed in the new location. The patient was then asked to walk 20 meters with the device and reported reduction of pain from 4/10 to 1/10. A further 1-2 mm posterior calibration of the left posterior BP reduced the pain to a level of 0/10. The patient did not report pain in his knees during gait assessment.

Heel-Rise Timing: Patient was asked to walk 20 m in order to confirm that he is still balanced and the heel-rise is well timed in the gait cycle. It was noted that the patient had a late heel-rise in both right and left leg. In order to correct this, a 2 mm hard spacer was fixed between the anterior BP's and the sole of both units, thus bringing the ankles into a more dorsi flexed position. The patient was reassessed while walking with the device and it was noted that the timing of the heel-rise was normalized in both legs. In addition, the patient reported he felt more stable during gait and it was observed that his gait velocity has increased.

Treatment Plan: The patient was briefed with safety instructions and was asked to wear the device at home for 45 minutes a day on each day of the first week of the treatment. Out of this total wearing time he was instructed to spend an accumulative time of 8-10 minutes in weight bearing activities (walking or standing while performing daily routine). Patient was instructed to increase overall daily wearing time of the device by 15 minutes every week for the initial 6 weeks, reaching 2 hours of total wearing time with the device every day (reaching an accumulative weight bearing time of approximately 25-30 minutes). The patient was contacted by the phone after 6 weeks and reported that he felt his hip and knee pain were much better (maximum pain level was rated at 2/10 in both the knees and the hips). The patient also informed that he felt much more stable in his gait, and said he has been wearing the device indoors for 5 hours a day without difficulty or discomfort. He was then instructed to reduce the overall wearing time inside the house and to begin walking outside for 5 minutes a day. If feeling comfortable, he was instructed to increase the outdoor walking by 5 minutes a week. The patient was seen for follow up consultations and assessments at the treatment center 3 months after his first visit, 11 months after his first visit and 20 months after his first visit. Each follow up consultation consisted of a gait lab test, an interview performed by a therapist (including report of current symptom level rated on a VAS and report of difficulty in function), a clinical assessment of gait without and with the device as well as changes in the calibration of the device and a treatment plan for the duration of time till the next follow up.

Treatment Progression: As detailed above, the patient immediately reported a reduction in pain while walking with the device during the initial consultation. In the first follow up consultation he reported the pain level in his left hip and both his knees was reduced to maximum pain level of 1/10. He found walking and negotiating stairs much easier (difficulty level less than 1/10). He has been wearing the device for 3 hours a day indoors performing daily activities as well as walking outside with it for 20 minutes a day (accumulative weight bearing time with the device of 1.5 hours). Clinical gait assessment revealed better clearance during swing phase bilaterally. Computerized barefoot gait assessment showed improvement in gait velocity, bilateral step length and bilateral single limb support (Table 1). The convexity level of all four BP's was increased to C with hard resilience. Gait assessment with the device did not reveal any deviations and the patient reported he felt comfortable with the new calibration. He was instructed to continue wearing the device for three hours indoors and 20 minutes of outdoor walking in order to allow for an adjustment period to the new calibration. Starting from the second week following the follow up consultation he was asked to increase his outdoor walking by 5 minutes per week until he reached a maximum of 40 minutes of outdoor walking.

The second follow up consultation was performed 11 months after the initial consultation. The patient then reported he had no pain in his hip or his knees. He felt his gait was much more comfortable and stable and he rated his level of difficulty in function at 0/10. A barefoot gait lab test revealed an increase in gait velocity to 122.1 cm/sec. Step length has increased to 67.4 cm in the left leg and 65.6 cm in the right leg. Single limb support was increased bi-laterally to 38.1% in the left leg and 40.0% in the right leg (see Table 1). These values show that the patient had a more symmetrical gait since the difference between the step lengths and single limb supports of the right and left legs has decreased. A clinical gait assessment with the device did not reveal any deviations and the convexity level of all BP's was increased to D with a soft resilience. The patient was instructed to maintain his current activity level with the device.

The third follow up, which was carried out 20 months after the beginning of the treatment, showed the patient has maintained his level of function and pain (0/10 on a VAS scale for both). A barefoot gait lab test revealed an increase in gait velocity to 129.2 cm/sec. Step length in the left leg was 66.7 cm and 66.5 cm in the right leg. Single limb support 38.3% in the left leg and 39.8% in the right leg indicating better gait symmetry (see table 1). No further changes have been made to the calibration of the device and the patient was asked to continue his current use of the device in order to maintain his level of improvement. Following that the patient was seen regularly for follow up consultations at the treatment center twice a year.

TABLE 1

Patient's gait parameters

| Visit | Velocity (cm/sec) | Left step length (cm) | Right Step length (cm) | Left Single Limb Support (in % of step cycle) | Right Single Limb Support (in % of step cycle) |
| --- | --- | --- | --- | --- | --- |
| 1$^{st}$ (initial) | 104.5 | 58.6 | 60 | 35.5 | 38.3 |
| 2$^{nd}$ (first follow-up) | 107.5 | 61.4 | 60.7 | 36.2 | 37.7 |
| 3$^{rd}$ (second follow-up) | 122.1 | 67.4 | 65.6 | 38.1 | 40.0 |
| 4$^{th}$ (third follow-up) | 129.2 | 66.7 | 66.5 | 38.3 | 39.8 |

Example 2

Treatment of a Subject (Patient) Having a Relapsing-Remitting Multiple Sclerosis (MS)

A 37 years old female patient was presented to the treatment center, has been diagnosed with relapsing-remitting multiple sclerosis (MS) at the age of 27.

Case History: In the ten years since her diagnosis the patient has suffered four attacks, all of which included visual deficits (which later improved) and weakness in both legs. She has been receiving immuno-globulin therapy every 6 weeks. She reported low back pain for many years, but that pain has intensified since her gait has deteriorated due to the MS.

Physical Examination: On observation, the patient was standing with bilateral knee recurvatum and hyper lordosis, probably due to weakness of muscles. She was able to maintain balance while standing on one leg for 20 seconds (in both legs). Assessment of ranges of motion at the ankles, knees, hips and low back did not reveal any limitations and did not produce pain. Manual muscle testing showed bilateral weakness of the dorsiflexors (MMT-3 bilaterally). Clinical gait assessment showed that the patient was ambulating with extensor thrust and hyper extension in both knees. In addition, she was using circumduction bilaterally and lateral trunk lean to the right to improve clearance during the swing phase. During the gait assessment the patient reported low back pain which she rated as 3 out of 10 on VAS.

Imaging and Gait Lab: Gait lab results (Table 2, below) showed velocity of 87.5 cm/sec, single limb support of 38.3% in the left leg and 39.7% in the right leg. Step length: Left: 50.6 cm Right: 49.4 cm.

Therapy:

Bulbous Protuberances (BP's): Identical BP's with a low convexity (B) and hard resilience were attached and fixed to the patient's device under the hind foot and the forefoot of the right and left devices. In order to increase her stability and attempt to strengthen the stabilizing muscles around the pelvis, a weighted disc (100 grams) was inserted and fixed between the posterior BP's and the patient's device under the hind foot of the left and right units. In order to maintain a neutral ankle position, a hard 2 mm spacer and a soft 2 mm spacer were inserted and fixed between the sole of both units of the device and the anterior BP's.

Balancing Process: The patient's device was calibrated and fine-tuned during repeated clinical gait assessments. During this process, changes were made to the calibration in order to minimize the angle of eversion or inversion at the ankle during heel strike, loading response, mid-stance and toe-off.

Pain: In order to reduce the pain in the low back, both the posterior BP's were calibrated 2 mm in the posterior direction. The patient was then asked to walk with the device and reported the pain was reduced to 2 out of 10 on a VAS scale. The posterior BP's were then calibrated and fixed a further 2 mm more posterior and the patient's gait and pain level were reassessed. The patient stated that her back pain was completely alleviated.

Heel-Rise Timing: Patient was asked to walk 20 m in order to confirm that she is still balanced and the heel-rise is well timed in the gait cycle. There were no visible deviations of heel rise timing.

Treatment Plan: The patient was briefed with safety instructions and asked to wear the device at home for 30 minutes per day for the first week of the treatment. She was also instructed that due to the potentially progressive nature of her condition she should cease using the device in case of the appearance of any new symptoms and consult the treating clinician. Out of this total wearing time she was instructed to spend an accumulative time of 4-5 minutes in weight bearing activities. She was instructed to add 10 minutes to the overall daily wearing time of the device every week, so that she reached an hour of total wearing time with the device every day after a four weeks of treatment (reaching an accumulative weight bearing time of approximately 12-14 minutes). She was asked to return for a follow up consultation a month after the commencement of the treatment. The patient was seen for follow up consultations a month after the initial consultation, 5 months after the initial consultation and 13 months after the initial consultation.

Treatment Progression: As described above, the patient immediately reported a reduction in pain while walking with the device during the initial consultation. In the first follow up consultation she reported the pain in her low back was reduced while walking with the device as well as during times she was not using the device. She has been wearing the device for an hour a day indoors performing daily activities as well as walking outside for 10 minutes a day (accumulative weight bearing time with the system of 20 minutes). Clinical gait assessment revealed a bilateral reduction of the circumduction. Computerized barefoot gait assessment showed improvement in gait velocity (105.4 cm/sec), bilateral step length (left 55.9 cm, right 56.4 cm) and bilateral single limb support (left 40.0, right 40.1% of gait cycle, see table 2). Gait assessment with the device did not reveal any deviations and the patient reported she felt comfortable with the device. No changes were made to the calibration and the patient was instructed to increase her wearing time indoors by 10 minutes a week to a maximum of 3 hours (accumulative weight bearing time of 1 hour) and increase her outdoor walking by 5 minutes per week to a maximum of 30 minutes The second follow up consultation was performed 5 months after the initial consultation. The patient reported that her back pain was almost completely relieved and she seldom felt it bother her. She has been using the system for an inconsistent number of hours indoors (range 2-5 hours) due to the fact that her low back was less painful and as a result her motivation to use the system has decreased. A barefoot gait lab test revealed a further increase in step length to 57.75 cm in the left leg and 57.0 cm in the right leg. The other parameters have retained their previous improvements (Table 2). These values show that the patient had better neuromuscular control around the pelvis and low back enabling her to further increase the step length via increased rotation of the pelvis and lumbar spine. A barefoot clinical gait assessment showed decreased circumduction bilaterally and better control of the movement of the knees by decreased extensor thrust and hyper extension in both knees. Clinical gait assessment with the device did not reveal any deviations and the convexity level of all BP's was increased to C with soft resilience. Repeated gait assessment showed that the patient had a late heel rise bilaterally. The soft spacer in the anterior left and right BP's was changed to a hard spacer, bringing the ankles to a slightly more dorsi flexed position. A repeated gait assessment with the device showed that the timing of the heel rise was corrected bilaterally. The patient was instructed to maintain her current activity level with the device.

The third follow up was carried out 13 months after the commencement of treatment. The patient reported that she still had low back pain occasionally which seemed to be unrelated to the treatment or to her level of activity. She was wearing the device for many hours a day, both indoors and outdoors, and she felt most comfortable while using it. She reported that when she felt her low back pain increase she puts the device on and it relieved the pain in matter of minutes. A barefoot gait lab test revealed an increase in gait velocity to 117.7 cm/sec. Step length in the left leg was 59.6 cm and 60.3 cm in the right leg. Single limb support was 41.5% in the left leg and 42.0% in the right leg (Table 2). A barefoot clinical gait assessment did not reveal any further improvements in her gait. In order to try and improve her neuromuscular control the convexity level of all BP's was increased to D with sort resilience. A gait assessment with the system showed the patient had good control of the increased level of perturbation throughout the gait cycle and she was asked to maintain her current level of function with the device.

Following that the patient was seen regularly for follow up consultations at the treatment center twice a year.

TABLE 2

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| $1^{st}$ (initial) | 89.5 | 50.6 | 49.4 | 38.3 | 39.2 |
| $2^{nd}$ (first follow-up) | 105.4 | 55.9 | 56.4 | 40.0 | 40.1 |
| $3^{rd}$ (second follow-up) | 105.3 | 57.8 | 57.0 | 39.9 | 40.8 |
| $4^{th}$ (third follow-up) | 117.7 | 59.7 | 60.3 | 41.5 | 42.0 |

Example 3

Treatment of a Subject (Patient) Having Spastic Diplegia

A 16 years old male patient presented to the treatment center, has been diagnosed with spastic diplegia due to cerebral palsy.

Case History: The patient was born prematurely on the 32nd week of an otherwise normal pregnancy, due to preeclampsia. He was diagnosed as suffering from cerebral palsy (spastic diplegia) at the age of 17 months. He arrived at the treatment center on a wheelchair since, as he reported, he fatigues very quickly when walking. Inside his home he reported he was able to walk independently for short distances. He reported that when he walked for more than 10 minutes he started to experience bilateral knee and low back pain. His treating orthopedic surgeon recommended a derotation osteotomy of the right femur, but declared that the patient must first improve his strength and level of function.

Physical Examination: On observation, the patient was obese and bears significantly more weight on his left leg. A typical crouch stance was observed including knee valgus, bilateral knee flexion (30 degrees on the right and 20 degrees on the left) and out toeing (right 70 degrees, left 20 degrees). Assessment of range of motion revealed a limitation of right knee extension (−10 degrees) as well as torsion of the right femur towards internal rotation. Functionally, he was unable to maintain balance on one leg on either the left or the right leg. There was a marked extensor hypertonia of the lower limbs, predominantly on the right. Clinical gait assessment showed a spastic gait without clearance of the right foot in swing, excessive right trunk rotation and forward trunk lean. During the gait assessment the patient did not report any pain but did report fatigue at the end of the process.

Imaging and Gait Lab: Gait lab results (Table 3) showed velocity of 86 cm/sec, single limb support of 32.3% in the left leg and 29.5% in the right leg. Step length: Left: 45.0 cm Right: 54.0 cm.

Treatment:

Bulbous Protuberances (BP's): Due to the patients' evident weakness and balancing abilities it was decided to use BP's of larger circumference (95 mm). These BP's have matching rubber caps with the same levels of convexity and degrees of resilience used in the BP's with smaller circumference (85 mm). Identical BP's with a low convexity (B) and soft resilience were attached and fixed to the patient's device under the hind foot and the forefoot of the right and left units.

Balancing Process: The patient's device was calibrated and fine-tuned during repeated clinical gait assessments. During this process, changes are made to the calibration in order to minimize the angle of eversion or inversion at the ankle during heel strike, loading response, mid-stance and toe-off. During this process, the treating clinician could not achieve a balanced position in the left ankle. Therefore, it was decided to reduce the convexity level of the rubber cap of the left posterior BP, and the B cap was replaced with an A cap. This brought the ankle to a slightly dorsi flexed position since A caps are lower than B caps. To compensate for this, two hard spacers were inserted and fixed between the left posterior BP and the sole of the left foot device. In addition, due to the severe hyper pronation of the right ankle a medial support was inserted and fixed between the right posterior BP and the sole of the right foot device. After these changes to the calibration the gait was reassessed and it was deemed that a balanced position was reached in both the left and the right ankles.

Pain: since the patient did not report pain during the clinical gait assessment, this stage was not performed.

Heel-Rise Timing: Patient was asked to walk 20 m in order to confirm that he is balanced and the heel-rise is well timed in the gait cycle. There were no visible deviations of heel rise timing.

Treatment Plan: The patient was briefed with safety instructions and was asked to wear the system at home for 60 minutes per day for the first week of the treatment. Out of this total wearing time he was asked to spend an accumulative amount of 10 minutes in weight bearing activities. He was asked to add 15 minutes to overall daily wearing time of the system, so that after a month he would reach two hours of total wearing time per day (reaching an accumulative weight bearing time of approximately 20 minutes). The first follow up consultation was planned a month after the beginning of the treatment. The patient was seen for follow up consultations a month after the initial consultation and 3 months after the initial consultation.

Treatment Progression: In the first follow up consultation the patient reported he felt ambulating with the device was considerably easier than without it. He has reached a total wearing time of two hours. He also reported that he noticed he fatigues less quickly when walking, though he was still very limited at any weight bearing activity. Computerized barefoot gait assessment showed a marked improvement in gait velocity (110 cm/sec). Step length increased significantly to 58.3 cm in the left leg and 65.2 cm in the right leg. Single limb support has also increased bilaterally (left 37.3, right 30.9% of gait cycle, see table 3). Clinical gait assessment showed a small decrease in right trunk rotation and forward trunk lean with no significant improvement of clearance during right swing. No changes were made to the calibration and the patient was instructed to increase his wearing time indoors by 15 minutes a week to a maximum of 4 hours as well as increase the relative percentage of weight bearing time (to a maximum of 1 hour).

The second follow up consultation was performed 3 months after the initial consultation. The patient reported that his level of activity has increased by 50% and he uses the device whenever he is at home. He also reported then he is now able to walk for over 20 minutes and he does not experience back or knee pain. As a result of the marked improvement in his functional status he has ceased the use of his wheelchair and he lost weight. A barefoot gait lab test showed better symmetry of single limb support (left 35.6, right 31.3% of gait cycle). The other parameters have retained their previous improvements (see table 3). A barefoot clinical gait assessment showed a marked reduction in trunk movements and improved clearance in the right swing. Clinical gait assessment with the device revealed a bilateral early heel rise. In order to correct this, a hard 2 mm spacer was inserted and fixed between the posterior BP's and the sole of both the left and the right foot units. Repeated gait assessment showed that the patient still had an early heel rise bilaterally. In order to correct this, another hard 2 mm spacer was introduced to both posterior BPs of the left and the right foot units. After this, the timing of the heel rise was normalized bilaterally. In order to increase the training effect of the device, the level of perturbation of the left posterior BP was increased by replacing the A cap with a B cap (higher level of convexity). A repeated gait assessment with the device showed that the timing of the heel rise was corrected bilaterally and no other gait deviations were apparent. The patient was instructed to maintain his current activity level with the device.

Following the described treatment, the patient was seen regularly for follow up consultations at the treatments center twice a year.

TABLE 3

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1st (initial) | 86.0 | 45.0 | 54.0 | 32.3 | 29.5 |
| 2nd (follow-up) | 110.0 | 58.0 | 65.0 | 37.3 | 30.9 |
| 3rd (follow-up) | 102.0 | 55.0 | 64.0 | 35.6 | 31.3 |

These examples present the unexpected benefit of the device in treating and improving/restoring neurological function in subjects suffering from various neurological conditions.

Example 4

Treatment of a Subject (Patient) Having Hemiparesis Post Cerebral Vascular Accident (CVA)

A 72 years old male patient was presented to the treatment center. The patient suffered from cerebrovascular accident (CVA) and was afflicted with right hemiparesis.

Case History: 6 months prior to the patient's arrival to the treatment center. The patient suffered a left CVA which resulted in right hemiparesis. He was hospitalized for a week following the stroke and was then admitted to a rehabilitation center for four weeks. Then he was treated in the community with physiotherapy and occupational therapy.

Upon his arrival to the clinic, the patient reported that he is limited to 20 minutes of outdoor walking due to fatigue in his right leg. He was able to ascend stairs in a non-reciprocal manner, leading with his left leg. He also reported of gait instability while walking in dimly lit surroundings or while walking on uneven ground. Due to this difficulty in balance he was intermittently using a walking stick.

Physical Examination: On observation, the patient was standing with increased weight bearing on the left leg, his right elbow flexed to 30 degrees and his right hand closed to a fist. The right leg was in 15 degrees of knee flexion with the ankle plantar flexed so that the heel was constantly off the ground. He was unable to perform a one leg stand on the right leg due to a balance deficit and was able to maintain a one leg stand on the left leg for only 5 seconds. The patient was then asked to go up and down stairs but was unable to do so in a reciprocal manner. During this activity an increase in extensor muscle tone was observed in the right leg, with the knee performing an extensor thrust and hyper extension. Assessment of ranges of motion at the ankles, knees, hips and low back did not reveal any limitations and did not produce pain. Manual muscle testing showed weakness of the right dorsiflexors (MMT-4) and quadriceps (MMT-4). Clinical computerized gait assessment showed that the patient was walking with increased extensor muscle tone in the right leg resulting in extensor thrust and hyper extension of the right knee. In addition, the patient had a functional weakness of the dorsiflexors in the right leg resulted in poor clearance during swing and foot slap during the loading response. As a result, he was circumducting his right leg during the swing phase.

Imaging and Gait Lab: Gait lab results (see table A) showed a slow walking velocity of 44 cm/sec, significantly reduced single limb support of 29.1% in the right leg and elevated single limb support of 42.7% in the left leg. Step length was also asymmetrical with a left step length of 40 cm and a right step length of 45 cm.

Therapy:

Bulbous Protuberances (BP's): In order to increase the weight bearing on the paretic right leg different levels of convexity were attached to the BPs of the right and left devices. A "B" level convexity with hard resilience was attached to the anterior and posterior BPs of the left leg. An "A" level convexity was attached to the anterior and posterior BPs of the right leg. The right BPs were also wider to further stimulate weight bearing on the right (95 mm in diameter as opposed to 85 mm in diameter of the left BP's). The 95 mm BPs with "A" caps have the same height as the 85 mm BP's with the "B" caps. In order to assist the clearance during right swing additional height needed to be added to the left BPs. Two hard spacers were therefore inserted and fixed between the left anterior and posterior BP's and the device.

Balancing Process: The patient's device was calibrated and fine-tuned during repeated clinical gait assessments. During this process, changes were made to the calibration in order to minimize the angle of eversion or inversion at the ankle during heel strike, loading response, mid-stance and toe-off. During this process the patient already began walking with better clearance during right swing and has a better knee control during right stance. The patient also reported that he felt more balanced with the device compared to his own shoes.

Heel-Rise Timing: Patient was asked to walk 20 meters in order to confirm that he is still balanced and the heel-rise is well timed in the gait cycle. There were no visible deviations of heel rise timing.

Gait Lab with the Device: A repeated gait lab test was performed with the patient wearing the device. The results showed a reduction of single limb support on the left leg indicating better clearance during the right swing phase (right 38.7%, left 29.8%). The step lengths were increased bilaterally and were symmetrical (51 cm bilaterally). The velocity has increased significantly to 61 cm/sec (see table A for details).

Treatment Plan: The patient was briefed with safety instructions and was asked to wear the device at home for an hour per day for the first week of the treatment. He was instructed to be in weight bearing for an accumulative time of 15 minutes (25% of the total wearing time) in short 1-4 minutes intervals each time. The patient was instructed to add 10 minutes to the overall daily wearing time of the device every week, while maintaining the accumulative 25% of weight bearing time. He was asked to return for a follow up consultation three weeks after the commencement of the treatment. The patient was seen for follow up consultations three weeks after the initial consultation, 3 months after the initial consultation and 6 months after the initial consultation.

Treatment Progression: As described above, the patient immediately reported an increase in comfort and sense of stability while walking with the device during the initial consultation. This was evident in the results of the gait lab as well. In the first follow up consultation he reported that he has been wearing the device indoors for an hour and a half each day, performing daily activities (accumulative weight bearing time with the device of about 18 minutes). Learning was evident as computerized barefoot gait assessment showed improvement in gait velocity (47 cm/sec), bilateral step length (left 41 cm, right 45 cm) with better step length symmetry and an improvement in single limb support symmetry (left 42.0, right 30.1% of gait cycle, see table A). Clinical gait assessment revealed a mild improvement in knee control during right stance phase, seen as a decrease in extensor thrust. A reduction in right circumduction was also noted. Gait assessment with the device did not reveal any deviations and the patient reported he felt comfortable with the device. No changes were made to the calibration and the patient was instructed to further increase his indoors wearing time by 15 minutes every week to a maximum of 3 hours (accumulative weight bearing time of 45 minutes).

The second follow up consultation was performed 3 months after the initial consultation. The patient reported that he has been using the device for three hours a day performing his daily indoors activities. He also reported that he started to perform some indoor continuous walking for 5 minutes. The patient also reported that he felt that walking and standing balance improved even while using his street shoes. A barefoot gait lab test revealed a further increase in step length to 46.2 cm in the left leg and 42.7 cm in the right leg. Single limb support in the right leg has increased to 31.0% and decreased in the left leg to 41.8%. Both the step lengths and the values of single limb support indicate better symmetry between the legs (which increase balance during all phases of gait). Gait velocity has also improved (Table A). A barefoot clinical gait assessment showed decreased circumduction on the right and better control of the movement of the right knee indicated by decreased extensor thrust and hyper extension. In addition, a decrease in the foot slap of the right foot was observed. Clinical gait assessment with the device did not reveal any deviations and the convexity level of the left BPs was increased to C with hard resilience. The level of convexity of the right anterior and posterior BPs was also increased from "A" to "B". Repeated gait assessment showed that the patient was controlling the increased convexity well. The patient was instructed to increase his total wearing time by 15 minutes each week to a maximum of 4 hours. He was also encouraged to try to increase his continuous walking by 1-2 minutes every week.

The third follow up was carried out 3 months after the commencement of treatment. At this time the patient reported that he was wearing the device for 5-6 hours a day and felt most comfortable while using it. He bought a treadmill and wanted to start doing his continuous walking on the treadmill. A barefoot gait lab test showed an increase in gait velocity to 55 cm/sec. Step length in the left leg was 45.0 cm and 48.0 cm in the right leg. Single limb support was 41.5% in the left leg and 31.5% in the right leg (Table 4). A barefoot clinical gait assessment revealed further improvements of the same parameters which improved in previous follow up consultations (right knee control, right clearance and circumduction). In order to further improve his neuromuscular control as well as strengthen the muscles of the right leg a weighted disc (100 grams) was inserted and fixed at the base of the left and right posterior BPs. A reassessment of the patients gait with the device showed he had a late heel rise in both legs. This was thought to be a result of the plantar flexed position which the insertion of the weighted disc has caused. A hard spacer and a soft spacer were inserted and fixed at the base of the left and the right anterior BPs. A reassessment of the patients gait with the device showed that the late heel rise was corrected by the new calibration. The patient was then asked to walk on a treadmill at a self-selected speed while the treating therapist was monitoring the process in order to ascertain the safety of this activity. When the therapist was satisfied that this activity was indeed safe for the patient he provided the patient with a treatment plan. The patient was instructed to continue his indoor use of the device while performing indoor activities. He was also instructed to walk on the treadmill at a comfortable speed for 10 minutes a day. He was instructed to increase walking time by 2-3 minutes a week. He was also advised to stop walking if he felt tired or unstable.

Then the patient was seen regularly for follow up consultations at the treatment center twice a year.

TABLE 4

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1$^{st}$ (initial) | 44 | 40 | 45 | 42.7 | 29.1 |
| 1$^{st}$ consult. with device | 61 | 51 | 51 | 38.7 | 29.8 |
| 2$^{nd}$ (first follow-up) | 47 | 41 | 45 | 42.0 | 30.1 |
| 3$^{rd}$ (second follow-up) | 50 | 42.7 | 46.2 | 41.0 | 31.0 |
| 4$^{th}$ (third follow-up) | 55 | 45 | 48 | 41.5 | 31.5 |

Example 5

Treatment a Patient with Ataxia Due to a Traumatic Brain Injury (TBI)

A 26 years old male patient was presented to the treatment center. The patient was suffering from TBI and was left with ataxia.

Case History: A year prior to the patient's arrival to the treatment center, he was involved in a motor vehicle accident from which he suffered a severe head and chest trauma. He had to be resuscitated and the resultant anoxia caused a diffuse axonal injury. He was hospitalized for 4 weeks following the accident and underwent numerous surgical procedures. Then, the patient was admitted to a rehabilitation center for eight weeks and then treated in the community with physiotherapy, hydrotherapy and occupational therapy. The patient reported that currently his main difficulty is his poor balance during gait. This was a limiting factor to his every day basic activities including outdoor walking, and basic self-care activities such as dressing up.

Physical Examination: On observation, the patient was standing with a wide base of support. No legs malalignments were noted. A Romberg test revealed an increased postural sway with open eyes and an inability to maintain balance with eyes shut. He was unable to perform a one leg stand on either leg. The patient was then asked to go up and down stairs but was unable to do so without holding the banister. Assessment of ranges of motion at the ankles, knees, hips and low back did not reveal any limitations and did not produce pain. Manual muscle testing did not reveal any specific weaknesses. Increased reflex responses were obtained bilaterally. Sensory assessment showed that the deep sensation was decreased in both legs. Clinical gait assessment showed the patient was walking with a wide base and a forward trunk lean. He also had difficulty in maintaining a straight line.

Imaging and Gait Lab: Gait lab results (see table 5) showed a slow walking velocity of 78 cm/sec, low single limb support values of 33.8% in the left leg and 35.5% in the right leg. Step length was also reduced: left step length 42.3 cm and right step length 41.0.

Therapy: Bulbous Protuberances (BPs): Due to the patient's balance difficulties, it was decided to use wider BPs having a base of 95 mm diameter. Identical BPs with a low convexity (B) and hard resilience were attached and fixed to the patient's device under the hind foot and the forefoot of the right and left devices.

Balancing Process: The patient's device was calibrated and fine-tuned during repeated clinical gait assessments. During this process, changes were made to calibration in order to minimize the angle of eversion or inversion at the ankle during heel strike, loading response, mid-stance and toe-off. The patients gait at the conclusion of the balancing process showed a reduction in the width of his base of support but he still experienced a difficulty in maintaining a straight line. In an attempt to improve proprioceptive feedback, a weight disc was inserted under the left and right posterior BPs. In order to avoid a plantar flexed position of the ankles due to the introduction of the disc, a soft spacer and a hard spacer were inserted and fixed under the anterior left and right BPs. This brought the ankle to a neutral (flat) position.

Heel-Rise Timing: Patient was asked to walk 20 m in order to confirm that he is still balanced and heel-rise remained timed within the gait cycle. A late heel rise was observed bilaterally. To correct this, a hard spacer was inserted and fixed under the anterior left and right BPs. This brought the ankle to a more dorsi flexed position. The patient was then asked to walk 20 meters again and his heel rise got corrected. The patient reported that he felt comfortable with the device and found walking easier and safer/stable. His gait was observed to have a narrower base of support and he was apparently more balanced.

Gait Lab with the Device: A repeated gait lab test was performed with the patient wearing the device (see table 5). The results showed a significant increase in velocity and bilateral step length (velocity 96.8 cm/sec, left step length 48.1 cm, right step length 47.6 cm) as well as a better symmetry in single limb support (left 34.0%, right 34.7%).

Treatment Plan: The patient was briefed with safety instructions and asked to wear the device at home for two hours a day for the first week of the treatment. He was instructed to be in weight bearing for an overall time of half an hour (25% of the total wearing time) in short 4-5 minute intervals each time. The patient was instructed to add 15 minutes to the overall daily wearing time of the device every week, while maintaining the accumulative 25% of weight bearing time. The patient was seen for follow up consultations four weeks after the initial consultation, 2 months after the initial consultation and 4 months after the initial consultation.

Treatment Progression: As described above, the patient reported an increase in comfort and sense of stability/balance while walking with the device during the initial consultation. In the first follow up consultation he reported that he has been wearing the device indoors for three hours a day performing daily activities (accumulative weight bearing time with the device of about 45 minutes). A computerized barefoot gait assessment showed improvement in gait velocity (90 cm/sec), bilateral step length (left 50.8 cm, right 49.5 cm) with better step length symmetry and an improvement in single limb support values and symmetry (left 34.2, right 35.0% of gait cycle, see table B). The bare foot results signify the unexpected benefits of the device in correction via memory-motor memory and neuronal control memory. During the clinical gait assessment his gait was coupled with a narrower base support and he was able to maintain a straight line when walking. A Romberg test showed a reduction in postural sway with open eyes and he was able to maintain his balance with shut eyes for 5 seconds. Gait assessment with the device did not reveal any deviations and the patient reported that he felt comfortable with the device. In order to increase balance training, the convexity level of all BPs was increased to a "C". A repeated clinical gait assessment revealed that the patient gained control over this increased perturbation level and his gait was well balanced. The patient was then instructed to maintain wearing time and the accumulative weight bearing time for the next two weeks in order to allow gaining of full control of the increased balancing demand. He was then asked to further increase his indoors wearing time by 30 minutes a week to a maximum of 5 hours (accumulative weight bearing time of 75 minutes).

The second follow up consultation was performed 2 months following the initial consultation. The patient reported that he has been using the device for five hours a day performing his indoors daily activities. The patient also reported that he felt he had better balance while walking with his street shoes and in self-care activities. A barefoot gait lab test revealed a further increase in step length to 52.3 cm in the left leg and 51.8 cm in the right leg. Velocity has increased to 100 cm/sec. Single limb support in the right leg has increased to 35.8% and 36.0% in the left leg. An improvement in the symmetry of gait was indicated by the values of step lengths and single limb support (Table 5). A barefoot clinical gait assessment showed a further, de-novo, improvement in neuromuscular control during gait and the patient was also able to maintain his balance during a Romberg's test with eyes shut for 15 seconds. A gait assessment with the device revealed that the patient's gait was well balanced with the device. To further increase the positive effect, all BPs were replaced with 85 mm diameter base BPs having the same ("C") level of convexity. The remaining adjustments were left unchanged. The patient was asked to maintain the amount of time he was using the device.

The third follow up was carried out 4 months after the beginning of the treatment. The patient reported that he was wearing the device indoors for 5-6 hours a day. Contrary to instructions, he also used the device occasionally while walking outdoors. A barefoot gait lab test showed a further improvement, albeit mild, in all the gait parameters (see table 5). A barefoot clinical gait assessment did not show any further improvements from previous follow up consultation. However, the patient was now able to maintain balance for a full 30 seconds while performing the Romberg's test with his eyes shut. A gait assessment with the device showed his gait was balanced. The treating physiotherapist thought that the current calibration of the device produced a sufficient challenge for the patient gait and balance and therefore chose to maintain the current calibration. Then the patient was seen regularly for follow up consultations at the treatment center 2-3 times a year.

TABLE 5

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| $1^{st}$ (initial) | 78 | 42.3 | 41.0 | 33.8 | 35.5 |
| $1^{st}$ consult. with device | 96.8 | 48.1 | 47.6 | 34.0 | 34.7 |
| $2^{nd}$ (first follow-up) | 90 | 50.8 | 49.5 | 34.2 | 35.0 |
| $3^{rd}$ (second follow-up) | 100 | 52.3 | 51.8 | 35.3 | 36.0 |
| $4^{th}$ (third follow-up) | 103 | 53.0 | 54.2 | 35.5 | 35.9 |

What is claimed is:

1. A method of improving, restoring, or both neurological control in a subject in need thereof, comprising the steps of:
   (a) securing a device to a subject's foot, whereby said device comprises a foot securing means, a support member operably attached to said securing means, and a moveable anterior protuberance and a moveable posterior protuberance, said anterior protuberance and said posterior protuberance are ground engaging, said moveable anterior protuberance and said moveable posterior protuberance are moveable along the outer surface of the support member; wherein each of said moveable anterior protuberance and said moveable posterior protuberance comprise a base and a peak, wherein said base is positioned on a centerline of said support member, wherein said peak is positioned offset from said centerline of said support member;
   (b) calibrating said posterior protuberance and said anterior protuberance to: a balanced position, said balanced position comprises a position whereby said device provides a reduced inversion, a reduced eversion, or both to said subject's foot during stance phases; and
   (c) fixing said posterior protuberance and said anterior protuberance to said support member;
   thereby improving, restoring, or both neurological control in a subject in need thereof.

2. The method of claim 1, wherein said calibrating further comprises balancing timing of heel rise.

3. The method of claim 1, whereby said calibrating comprises adjusting: (a) a resilience of said anterior protuberance, said posterior protuberance, or a combination thereof; (b) a hardness of said anterior protuberance, said posterior protuberance, or a combination thereof; (c) an elasticity of said anterior protuberance, said posterior protuberance, or a combination thereof; (d) or any combination of (a), (b), and (c).

4. The method of claim 1, whereby said calibrating comprises adjusting a height of said anterior protuberance, said posterior protuberance, or a combination thereof; (b) a convexity of said anterior protuberance, said posterior protuberance, or a combination thereof; (c) a weight of said anterior protuberance, said posterior protuberance, or a combination thereof (d) and a combination of (a), (b), and (c).

5. The method of claim 1, whereby said balanced position further comprises a position whereby reduced valgus, varus, dorsal or plantar torque about the ankle is exerted by said device on said subject's foot.

6. The method of claim 1, whereby said posterior protuberance is a bulbous protuberance, said anterior protuberance is a bulbous protuberance, or both said posterior protuberance and said anterior protuberance are bulbous protuberances.

7. The method of claim 1, whereby said posterior protuberance is positioned within a calcaneus support portion of said support member.

8. The method of claim 1, whereby said anterior protuberance is positioned within phalanges or metatarsals support portion of said support member.

9. The method of claim 1, whereby said anterior protuberance, said posterior protuberance, or their combination comprise a cross-section with a shape of a conic section, said conic section comprising at least one of a circle, ellipse, parabola and hyperbola.

10. The method of claim 1, whereby said anterior protuberance is shaped differently from said posterior protuberance.

11. The method of claim 1, wherein the subject is afflicted with a neurological disorder.

12. The method of claim 11, wherein the neurological disorder is selected from stroke, cerebrovascular accident (CVA), ischemic CVA, hemorrhagic CVA, Traumatic Brain Injury (TBI), Anoxic Brain Damage (ABD), Cerebral Palsy (CP), Parkinson's disease (PD), Multiple Sclerosis (MS), Spinal Cord Injury (SCI), Charcot-Marry-Tooth (CMT), Guillain-Barré syndrome (GBS) and Poliomyelitis.

13. The method of claim 1, wherein the improvement in neurological control comprises improvement in gait parameters of the subject.

14. The method of claim 13, wherein the gait parameters are selected from: velocity, step length, single limb support, stability and combinations thereof.

* * * * *